United States Patent
Lienhard et al.

(10) Patent No.: US 7,799,538 B2
(45) Date of Patent: Sep. 21, 2010

(54) METHOD FOR IDENTIFYING AGENTS WHICH MODULATE GTPASE ACTIVITY INVOLVED IN INSULIN-STIMULATED GLUT4 TRANSLOCATION

(75) Inventors: Gustav E. Lienhard, Hanover, NH (US); Susan Kane, Beverly, MA (US); Cristinel P. Miinea, Whitehall, PA (US); Hiroyuki Sano, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 588 days.

(21) Appl. No.: 11/817,819

(22) PCT Filed: Mar. 8, 2006

(86) PCT No.: PCT/US2006/008336
§ 371 (c)(1),
(2), (4) Date: Sep. 5, 2007

(87) PCT Pub. No.: WO2006/099005
PCT Pub. Date: Sep. 21, 2006

(65) Prior Publication Data
US 2008/0268487 A1    Oct. 30, 2008

Related U.S. Application Data

(60) Provisional application No. 60/660,131, filed on Mar. 9, 2005.

(51) Int. Cl.
*C12Q 1/34* (2006.01)
(52) U.S. Cl. .......................... 435/18; 435/4

(58) Field of Classification Search .................. None
See application file for complete search history.

(56) References Cited

OTHER PUBLICATIONS

Bae et al., "Isoform-specific Regulation of Inuslin-dependent Glucose Uptake by Akt-Protein Kinase B", J. Biol. Chem. 2003 276(49):49530-49536.
Cormon et al., "Insulin and Okadaic Acid Induce Rab4 Redistribution in Adipocytes", J. Biol. Chem. 1993 266(26):19491-19497.
Jiang et al., "Insulin signaling through Akt/protein kinase B analyzed by small interfering RNA-mediated gene silencing", Proc. Natl. Acad. Sci. USA 2003 100(13):7569-7574.
Kane et al., "A Method to Identify Serine Kinase Substrates", J. Biol. Chem. 2002 277(25):22115-22118.
Katome et al., "Use of RNA Interference-mediated Gene Silencing and Adenoviral Overexpression to Elucidate the Roles of ATK/Protein Kinase B Isoforms in Insulin Actions", J. Biol. Chem. 2003 278(30):28312-28323.
Kessler et al., Rab11 is associated with GLUT4-containing vesicles and redistributes in response to insulin, Diabetologia 2000 43:1518-1527.
Sano et al., "Insulin-stimulated Phosphorylation of a Rab GTPase-activating Protein Regulates GLUT4 Translocation", J. Biol. Chem. 2003 278(17):14599-14602.
Watson et al., "Regulated Membrane Trafficking of the Insulin-Responsive Glucose Transporter 4 in Adipocytes", Endocrine Reviews 2004 25(2):177-204.
Zeigerer et al., "Insulin Stimulation of GLUT4 Exocytosis, but Not Its Inhibition of Endocytosis, Is Dependent on RabGAP AS160", Molecular Biology of the Cell 2004 15:4406-4415.

*Primary Examiner*—Herbert J. Lilling
(74) *Attorney, Agent, or Firm*—Licata & Tyrrell P.C.

(57) ABSTRACT

The present invention is a method for identifying agents that modulate the GTPase activity of AS160. In the instant assay, AS160 or the GAP domain thereof is contacted with a test agent, in the presence of GTP-bound Rab (2A, 8A, 8B, 10, or 14), and the AS160 GAP domain-mediated hydrolysis of GTP to GDP is monitored.

1 Claim, 4 Drawing Sheets

```
            1          β1                  α1                    β2   50
2A     .....MAYAY  LFKYIIIGDT  GVGKSCLLLQ  FTDKRFQPVH  DLTIGVEFGA
14     MATAPYNYSY  IFKYIIIGDM  GVGKSCLLHQ  FTEKKFMADC  PHTIGVEFGT
8A     ...MAKTYDY  LFKLLLIGDS  GVGKTCVLFR  FSEDAFNSTF  ISTIGIDFKI
8B     ...MAKTYDY  LFKLLLIGDS  GVGKTCLLFR  FSEDAFNTTF  ISTIGIDFKI
10     ..MAKKTYDL  LFKLLLIGDS  GVGKTCVLFR  FSDDAFNTTF  ISTIGIDFKI
Rab    .....xxYxy  lFKyiiIGDx  GVGKsClLxq  Ft#kxFxxxx  xxTIG!#Fgx
                       PM1                    G1          PM2

51 β2           β3            α2          β4         α3  100
2A     RMITIDGKQI  KLQIWDTAGQ  ESFRSITRSY  YRGAAGALLV  YDITRRDTFN
14     RIIEVSGQKI  KLQIWDTAGQ  ERFRAVTRSY  YRGAAGALMV  YDITRRSTYN
8A     RTIELDGKRI  KLQIWDTAGQ  ERFRTITTAY  YRGAMGIMLV  YDITNEKSFD
8B     RTIELDGKKI  KLQIWDTAGQ  ERFRTITTAY  YRGAMGIMLV  YDITNEKSFD
10     KTVELQGKKI  KLQIWDTAGQ  ERFHTITTSY  YRGAMGIMLV  YDITNGKSFE
Rab    rx!exdGkkI  KLQIWDTAGQ  ErFrx!TrsY  YRGAaGa$$V  YDITrrxt%#
                       PM3

101  α3           β5                α4              150
2A     HLTTWLEDAR  QHSNSNMVIM  LIGNKSDLES  RREVKKEEGE  AFAREHGLIF
14     HLSSWLTDAR  NLTNPNTVII  LIGNKADLEA  QRDVTYEEAK  QFAEENGLLF
8A     NIRNWIRNIE  EHASADVEKM  ILGNKCDVND  KRQVSKERGE  KLALDYGIKF
8B     NIKNWIRNIE  EHASSDVERM  ILGNKCDMND  KRQVSKERGE  KLAIDYGIKF
10     NISKWLRNID  EHANEDVERM  LLGNKCDMDD  KRVVPKGKGG  QIAREHGIRF
Rab    hlxxWlx#ar  #hxnx#xvim  liGNKxDl#x  xRxVxkeege  xfAx#xGlxF
                                    G2

151 β6                α5                              200
2A     METSAKTASN  VEEAFINTAK  EIYEKIQEGV  FDINNEANGI  KIGPQHAATN
14     LEASAKTGEN  VEDAFLEAAK  KIYQNIQDGS  LDLNAAESGV  QHKPS.APQG
8A     METSAKANIN  VENAFFTLAR  DIKAKMDKKL  EGNSPQGSNQ  GVKITPDQQK
8B     LETSAKSSAN  VEEAFFTLAR  DIMTKLNRKM  NDSNSAGAGG  PVKITENRSK
10     FETSAKANIN  IEKAFLTLAE  DILRKTPVKE  PNSENVDISS  GGGVTGWKSK
Rab    xEtSAKtxxN  !ExAFxxxAk  xIyxkiqxgx  xdxnxxxxgx  xxkpxxaxxx
         G3

201         217
2A     ATHAGNQGGQ  QAGGGCC    (SEQ ID NO:3)
14     GRLTSEPQPQ  REGCGC.    (SEQ ID NO:7)
8A     RSSFFRCVLL  .......    (SEQ ID NO:4)
8B     KTSFFRCSLL  .......    (SEQ ID NO:5)
10     CC........  .......    (SEQ ID NO:6)
Rab    xx........q  ..g.gc.   (SEQ ID NO:8)
```

FIG. 1

```
        1                                                              50
27B  MTDGDYDYLI  KLLALGDSGV  GKTTFLYRYT  DNKFNPKFIT  TVGIDFREKR
4A   MSQTAMSETY  DFLFKFLVIG  NAGTGKSCLL  HQFIEKKFKD  DSNHTIGVEF
11A  MGTRDDEYDY  LFKVVLIGDS  GVGKSNLLSR  FTRNEFNLES  KSTIGVEFAT
21   MAAAGGGGGG  AAAAGRAYSF  KVVLLGEGCV  GKTSLVLRYC  ENKFNDKHIT
2A   ..........  ......MAYA  YLFKYIIIGD  TGVGKSCLLL  QFTDKRFQPV
4B   ..........  ....MAEDRH  FLFKFLVIGS  AGTGKSC̄LLH  QFIENKFKQD
14   ..........  .MATAPYNYS  YIFKYIIIGD  MGVGKSC̄LLH  QFTEKKFMAD
11B  ..........  .MGTRDDEYD  YLFKVVLIGD  SGVGKSN̄LLS  RFTRNEFNLE
1A   ..........  .MSSMNPEYD  YLFKLLLIGD  SGVGKSCLLL  RFADDTYTES
1B   ..........  ....MNPEYD  YLFKLLLIGD  SGVGKSC̄LLL  RFADDTYTEN
8A   ..........  ....MAKTYD  YLFKLLLIGD  SGVGKTC̄VLF  RFSEDAFNST
27A  ..........  ...MSDGDYD  YLIKFLALGD  SGVGKTSVLY  QYTDGKFNSK
8B   ..........  ....MAKTYD  YLFKLLLIGD  SGVGKTCLLF  RFSEDAFNTT
10   ..........  ...MAKKTYD  LLFKLLLIGD  SGVGKTC̄VLF  RFSDDAFNTT
35   ..........  ....MARDYD  HLFKLLIIGD  SGVGKSS̄LLL  RFADNTFSGS
3A   MASATDSRYG  QKESSDQNFD  YMFKILIIGN  SSVGKTSFLF  RYADDSFTPA
3D   MASAGDTQAG  PRDAADQNFD  YMKLLLIGN   SSVGKTSFLF  RYADDSFTPA
18   ..........  ....MDEDVL  TTLKILIIGE  SGVGKSSLLL  RFTDDTFDPE
5A   MASRG.A.TR  PNGPNTGNKI  CQFKLVLLGE  SAVGKSSLVL  RFVKGQFHEF
5C   MAGRGGA.AR  PNGPAAGNKI  CQFKLVLLGE  SAVGKSSLVL  RFVKGQFHEY
5B   MTSRS.T.AR  PNGQPQASKI  CQFKLVLLGE  SAVGKSSLVL  RFVKGQFHEY
6A   .........M  STGGDFGNPL  RKFKLVFLGE  QSVGKTSLIT  RFMYDSFDNT
6B   .........M  SAGGDFGNPL  RKFKLVFLGE  QSVGKTSLIT  RFMYDSFDNT
7    ..........  ....MTSRKK  VLLKVIILGD  SGVGKTSLMN  QYVNKKFSNQ 51                                                             100
27B  VVYNAQGPNG  SSGKAFK...  .......VHL  QLWDTAGQER  FRSLTTAFFR
4A   GSKIINVGGK  YVKLQIW...  .......DTA  GQERFRSVTR  SYYRGAAGAL
11A  RSIQVDGKTI  KAQIWDT...  .......AGQ  ERYRAITSAY  YRGAVGALLV
21   TLQASFLTKK  LNIGGKR...  .......VNL  AIWDTAGQER  FHALGPIYYR
2A   HDLTIGVEFG  ARMITID...  .......GKQ  IKLQIWDTAG  QESFRSITRS
4B   SNHTIGVEFG  SRVVNVG...  .......GKT  VKLQIWDTAG  QERFRSVTRS
14   CPHTIGVEFG  TRIIEVS...  .......GQK  IKLQIWDTAG  QERFRAVTRS
11B  SKSTIGVEFA  TRSIQVD...  .......GKT  IKAQIWDTAG  QERYRAITSA
1A   YISTIGVDFK  IRTIELD...  .......GKT  IKLQIWDTAG  QERFRTITSS
1B   YISTIGVDFK  IRTIELD...  .......GKT  IKLQIWDTAG  QERFRTITSS
8A   FISTIGIDFK  IRTIELD...  .......GKR  IKLQIWDTAG  QERFRTITTA
27A  FITTVGIDFR  EKRVVYRASG  PDGATGRGQR  IHLQLWDTAG  QERFRSLTTT
8B   FISTIGIDFK  IRTIELD...  .......GKK  IKLQIWDTAG  QERFRTITTA
10   FISTIGIDFK  IKTVELQ...  .......GKK  IKLQIWDTAG  QERFHTITTS
35   YITTIGVDFK  IRTVEIN...  .......GEK  VKLQIWDTAG  QERFRTITST
3A   FVSTVGIDFK  VKTIYRN...  .......DKR  IKLQIWDTAG  QERYRTITTA
3D   FVSTVGIDFK  VKTVYRH...  .......DKR  IKLQIWDTAG  QERYRTITTA
18   LAATIGVDFK  VKTISVD...  .......GNK  AKLAIWDTAG  QERFRTLTPS
5A   QESTIGAAFL  TQTVCLD...  .......DTT  VKFEIWDTAG  QERYHSLAPM
5C   QESTIGAAFL  TQTVCLD...  .......DTT  VKFEIWDTAG  QERYHSLAPM
5B   QESTIGAAFL  TQSVCLD...  .......DTT  VKFEIWDTAG  QERYHSLAPM
6A   YQATIGIDFL  SKTMYLE...  .......DRT  IRLQLWDTAG  QERFRSLIPS
6B   YQATIGIDFL  SKTMYLE...  .......DRT  VRLQLWDTAG  QERFRSLIPS
7    YKATIGADFL  IKEVMVD...  .......DRL  VTMQIWDTAG  QERFQSLGVA
```

*FIG. 2A*

```
        101                                                      150
27B DAMGFLLMFD LTSQQSFLNV RNWMSQLQAN AYCENPDIVL IGNKADLPDQ
4A  LVYDITSRET YNALTNWLTD ARMLASQNIV IILCGNKKDL DADREVTFLE
11A YDIAKHLTYE NVERWLKELR DHADSNIVIM LVGNKSDLRH LRAVPTDEAR
21  DSNGAILVYD ITDEDSFQKV KNWVKELRKM LGNEICLCIV GNKIDLEKER
2A  YYRGAAGALL VYDITRRDTF NHLTTWLEDA RQHSNS...N .MVIMLIGNK
4B  YYRGAAGALL VYDITSRETY NSLAAWLTDA RTLASP...N .IVVILCGNK
14  YYRGAAGALM VYDITRRSTY NHLSSWLTDA RNLTNP...N .TVIILIGNK
11B YYRGAVGALL VYDIAKHLTY ENVERWLKEL RDHADS...N .IVIMLVGNK
1A  YYRGAHGIIV VYDVTDQESF NNVKQWLQEI DRYASE...N .VNKLLVGNK
1B  YYRGAHGIIV VYDVTDQESY ANVKQWLQEI DRYASE...N .VNKLLVGNK
8A  YYRGAMGIML VYDITNEKSF DNIRNWIRNI EEHASA...D .VEKMILGNK
27A FFRDAMGFLL LFDLTNEQSF LNVRNWISQL QMHAYC...E NPDIVLCGNK
8B  YYRGAMGIML VYDITNEKSF DNIKNWIRNI EEHASS...D .VERMILGNK
10  YYRGAMGIML VYDITNGKSF ENISKWLRNI DEHANE...D .VERMLLGNK
35  YYRGTHGVIV VYDVTSAESF VNVKRWLHEI NQNC.D...D .VCRILVGNK
3A  YYRGAMGFIL MYDITNEESF NAVQDWSTQI KTYSWD...N .AQVLLVGNK
3D  YYRGAMGFLL MYDIANQESF AAVQDWATQI KTYSWD...N .AQVILVGNK
18  YYRGAQGVIL VYDVTRRDTF VKLDNWLNEL ETYCTR...N DIVNMLVGNK
5A  YYRGAQAAIV VYDITNEESF ARAKNWVKEL QRQASP...N .IVIALSGNK
5C  YYRGAQAAIV VYDITNTDTF ARAKNWVKEL QRQASP...N .IVIALAGNK
5B  YYRGAQAAIV VYDITNQETF ARAKTWVKEL QRQASP...S .IVIALAGNK
6A  YIRDSAAAVV VYDITNVNSF QQTTKWIDDV RTERGS...D .VIIMLVGNK
6B  YIRDSTVAVV VYDITNLNSF QQTSKWIDDV RTERGS...D .VIIMLAGNK
7   FYRGADCCVL VFDVTAPNTF KTLDSWRDEF LIQASPRDPE NFPFVVLGNK 151                                                      200
27B REVNERQARE LADKYGIPYF ETSAATGQNV EKAVETLLDL IMKRMEQCVE
4A  ASRFAQENEL MFLETSALTG ENVEEAFVQC ARKILNKIES GELDPERMGS
11A AFAEKNGLSF IETSALDSTN VEAAFQTILT EIYRIVSQKQ MSDRRENDMS
21  HVSIQEAESY AESVGAKYH TSAKQNKGIE ELFLDLCKRM IETAQVDERA
2A  SDLESRREVK KEEGEAFARE HGLIFMETSA KTASNVEEAF INTAKEIYEK
4B  KDLDPEREVT FLEASRFAQE NELMFLETSA LTGENVEEAF LKCARTILNK
14  ADLEAQRDVT YEEAKQFAEE NGLLFLEASA KTGENVEDAF LEAAKKIYQN
11B SDLRHLRAVP TDEARAFAEK NNLSFIETSA LDSTNVEEAF KNILTEIYRI
1A  CDLTTKKVVD YTTAKEFADS LGIPFLETSA KNATNVEQSF MTMAAEIKKR
1B  SDLTTKKVVD NTTAKEFADS LGIPFLETSA KNATNVEQAF MTMAAEIKKR
8A  CDVNDKRQVS KERGEKLALD YGIKFMETSA KANINVENAF FTLARDIKAK
27A SDLEDQRVVK EEEAIALAEK YGIPYFETSA ANGTNISQAI EMLLDLIMKR
8B  CDMNDKRQVS KERGEKLAID YGIKFLETSA KSSANVEEAF FTLARDIMTK
10  CDMDDKRVVP KGKGEQIARE HGIRFFETSA KANINIEKAF LTLAEDILRK
35  NDDPERKVVE TEDAYKFAGQ MGIQLFETSA KENVNVEEMF NCITELVLRA
3A  CDMEDERVVS SERGRQLADH LGFEFFEASA KDNINVKQTF ERLVDVICEK
3D  CDLEDERVVP AEDGRRLADD LGFEFFEASA KENINVKQVF ERLVDVICEK
18  ID.KENREVD RNEGLKFARK HSMLFIEASA KTCDGVQCAF EELVEKIIQT
5A  ADLANKRAVD FQEAQSYADD NSLLFMETSA KTSMNVNEIF MAIAKKLPKN
5C  ADLASKRAVE FQEAQAYADD NSLLFMETSA KTAMNVNEIF MAIAKKLPKN
5B  ADLANKRMVE YEEAQAYADD NSLLFMETSA KTAMNVNDLF LAIAKKLPKS
6A  TDLADKRQVS IEEGERKAKE LNVMFIETSA KAGYDVKQLF RRVAAALPGM
6B  TDLADKRQIT IEEGEQRAKE LSVMFIETSA KTGYNVKQLF RRVASALPGM
7   IDLENRQVAT KRAQAWCYSK NNIPYFETSA KEAINVEQAF QTIARNALKQ
```

*FIG. 2B*

```
                                                                    SEQ ID
                                                                    NO:
       201                                            245
27B  KTQIPDTVNG  GNSGNLDGEK  PPEKKCIC..  ..........  .....     10
4A   GIQYGDAALR  QLRSPRRAQA  PNAQECGC..  ..........  .....     11
11A  PSNNVVPIHV  PPTTENKPKV  QCCQNI....  ..........  .....     12
21   KGNGSSQPGT  ARRGVQIIDD  EPQAQTSGGG  CCSSG.....  .....     13
2A   IQEGVFDINN  EANGIKIGPQ  HAATNATHAG  NQGGQQAGGG  CC...      3
4B   IDSGELDPER  MGSGIQYGDA  SLRQLRQPRS  AQAVAPQPCG  C....     14
14   IQDGSLDLNA  AESGVQHKPS  APQGGRLTSE  PQPQR.EGCG  C....      7
11B  VSQKQIADCA  AHD..ESPGN  NVVDISVPPT  TDGQKPNKLQ  CCQNL     15
1A   MGPGATAGGA  EKSNVKIQST  PVKQSGGGCC  ..........  .....     16
1B   MGPGAASGG.  ERPNLKIDST  PVKPAGGGCC  ..........  .....     17
8A   MDKKLEGNSP  QGSNQGVKIT  PDQQKRSSFF  RCVLL.....  .....      4
27A  MERCVDKSWI  PEGVVRSNGH  ASTDQL....  SEEKEKGACG  C....     18
8B   LNRKMNDSNS  AGAGGPVKIT  ENRSKKTSFF  RCSLL.....  .....      5
10   TPVKEPNSEN  VDISSGGGVT  GWKSKCC...  ..........  .....      6
35   KKDNLAKQQQ  QQQNDVVKLT  KNSKRKKRCC  ..........  .....     19
3A   MSESLDTADP  AVTGAKQGPQ  LSDQQVPPHQ  DCAC......  .....     20
3D   MNESLEPSSS  SGSNGK.GPA  VGDAPAPQPS  SCSC......  .....     21
18   PGLWESENQN  KGVKLSHREE  GQGGGACGGY  CSVL......  .....     22
5A   EP.QNPGANS  ARGRGVDLTE  PTQPTRNQCC  SN........  .....     23
5C   EP.QNATGAP  GRNRGVDLQE  NNPASRSQCC  SN........  .....     24
5B   EP.QNLGGAA  GRSRGVDLHE  QSQQNKSQCC  SN........  .....     25
6A   ESTQDRSRED  MIDIKLEKPQ  EQPVSEGGCS  C.........  .....     26
6B   ENVQEKSKEG  MIDIKLDKPQ  EPPASEGGCS  C.........  .....     27
7    ETEEELYNEF  PEPIKLDKND  RAKASAESCS  C.........  .....     28
```

FIG. 2C

SEQUENCE LISTING

```
<160> NUMBER OF SEQ ID NOS: 28

<210> SEQ ID NO 1
<211> LENGTH: 1299
<212> TYPE: PRT
<213> ORGANISM: Homo sapiens

<400> SEQUENCE: 1

Met Glu Pro Pro Ser Cys Ile Gln Asp Glu Pro Phe Pro His Pro Leu
1               5                   10                  15

Glu Pro Glu Pro Gly Val Ser Ala Gln Pro Gly Pro Gly Lys Pro Ser
            20                  25                  30

Asp Lys Arg Phe Arg Leu Trp Tyr Val Gly Gly Ser Cys Leu Asp His
        35                  40                  45

Arg Thr Thr Leu Pro Met Leu Pro Trp Leu Met Ala Glu Ile Arg Arg
    50                  55                  60

Arg Ser Gln Lys Pro Glu Ala Gly Gly Cys Gly Ala Pro Ala Ala Arg
65                  70                  75                  80

Glu Val Ile Leu Val Leu Ser Ala Pro Phe Leu Arg Cys Val Pro Ala
                85                  90                  95

Pro Gly Ala Gly Ala Ser Gly Gly Thr Ser Pro Ser Ala Thr Gln Pro
            100                 105                 110

Asn Pro Ala Val Phe Ile Phe Glu His Lys Ala Gln His Ile Ser Arg
        115                 120                 125

Phe Ile His Asn Ser His Asp Leu Thr Tyr Phe Ala Tyr Leu Ile Lys
    130                 135                 140

Ala Gln Pro Asp Asp Pro Glu Ser Gln Met Ala Cys His Val Phe Arg
145                 150                 155                 160

Ala Thr Asp Pro Ser Gln Val Pro Asp Val Ile Ser Ser Ile Arg Gln
                165                 170                 175

Leu Ser Lys Ala Ala Met Lys Gly Asp Ala Lys Pro Ser Lys Asp Asn
            180                 185                 190

Glu Asp Ala Phe Tyr Asn Ser Gln Lys Phe Glu Val Leu Tyr Cys Gly
        195                 200                 205
```

-continued

```
Lys Val Thr Val Thr His Lys Ala Pro Ser Ser Leu Ile Asp Asp
    210                 215                 220
Cys Met Glu Lys Phe Ser Leu His Glu Gln Gln Arg Leu Lys Ile Gln
225                 230                 235                 240
Gly Glu Gln Arg Gly Pro Asp Pro Gly Glu Asp Leu Ala Asp Leu Glu
                245                 250                 255
Val Val Val Pro Gly Ser Pro Gly Asp Cys Leu Pro Glu Glu Ala Asp
            260                 265                 270
Gly Thr Asp Thr His Leu Gly Leu Pro Ala Gly Ala Ser Gln Pro Ala
        275                 280                 285
Leu Thr Ser Ser Arg Val Cys Phe Pro Glu Arg Ile Leu Glu Asp Ser
290                 295                 300
Gly Phe Asp Glu Gln Gln Glu Phe Arg Ser Arg Cys Ser Ser Val Thr
305                 310                 315                 320
Gly Val Gln Arg Arg Val His Glu Gly Ser Gln Lys Ser Gln Pro Arg
                325                 330                 335
Arg Arg His Ala Ser Ala Pro Ser His Val Gln Pro Ser Asp Ser Glu
            340                 345                 350
Lys Asn Arg Thr Met Leu Phe Gln Val Gly Arg Phe Glu Ile Asn Leu
        355                 360                 365
Ile Ser Pro Asp Thr Lys Ser Val Val Leu Glu Lys Asn Phe Lys Asp
370                 375                 380
Ile Ser Ser Cys Ser Gln Gly Ile Lys His Val Asp His Phe Gly Phe
385                 390                 395                 400
Ile Cys Arg Glu Ser Pro Glu Pro Gly Leu Ser Gln Tyr Ile Cys Tyr
                405                 410                 415
Val Phe Gln Cys Ala Ser Glu Ser Leu Val Asp Glu Val Met Leu Thr
            420                 425                 430
Leu Lys Gln Ala Phe Ser Thr Ala Ala Ala Leu Gln Ser Ala Lys Thr
        435                 440                 445
Gln Ile Lys Leu Cys Glu Ala Cys Pro Met His Ser Leu His Lys Leu
450                 455                 460
Cys Glu Arg Ile Glu Gly Leu Tyr Pro Pro Arg Ala Lys Leu Val Ile
465                 470                 475                 480
Gln Arg His Leu Ser Ser Leu Thr Asp Asn Glu Gln Ala Asp Ile Phe
                485                 490                 495
Glu Arg Val Gln Lys Met Lys Pro Val Ser Asp Gln Glu Glu Asn Glu
            500                 505                 510
Leu Val Ile Leu His Leu Arg Gln Leu Cys Glu Ala Lys Gln Lys Thr
        515                 520                 525
His Val His Ile Gly Glu Gly Pro Ser Thr Ile Ser Asn Ser Thr Ile
530                 535                 540
Pro Glu Asn Ala Thr Ser Ser Gly Arg Phe Lys Leu Asp Ile Leu Lys
545                 550                 555                 560
Asn Lys Ala Lys Arg Ser Leu Thr Ser Ser Leu Glu Asn Ile Phe Ser
                565                 570                 575
Arg Gly Ala Asn Arg Met Arg Gly Arg Leu Gly Ser Val Asp Ser Phe
            580                 585                 590
Glu Arg Ser Asn Ser Leu Ala Ser Glu Lys Asp Tyr Ser Pro Gly Asp
        595                 600                 605
Ser Pro Pro Gly Thr Pro Pro Ala Ser Pro Pro Ser Ser Ala Trp Gln
610                 615                 620
```

```
Thr Phe Pro Glu Glu Asp Ser Asp Ser Pro Gln Phe Arg Arg Arg Ala
625                 630                 635                 640

His Thr Phe Ser His Pro Pro Ser Ser Thr Lys Arg Lys Leu Asn Leu
            645                 650                 655

Gln Asp Gly Arg Ala Gln Gly Val Arg Ser Pro Leu Leu Arg Gln Ser
        660                 665                 670

Ser Ser Glu Gln Cys Ser Asn Leu Ser Ser Val Arg Arg Met Tyr Lys
        675                 680                 685

Glu Ser Asn Ser Ser Ser Ser Leu Pro Ser Leu His Thr Ser Phe Ser
    690                 695                 700

Ala Pro Ser Phe Thr Ala Pro Ser Phe Leu Lys Ser Phe Tyr Gln Asn
705                 710                 715                 720

Ser Gly Arg Leu Ser Pro Gln Tyr Glu Asn Glu Ile Arg Gln Asp Thr
            725                 730                 735

Ala Ser Glu Ser Ser Asp Gly Glu Gly Arg Lys Arg Thr Ser Ser Thr
        740                 745                 750

Cys Ser Asn Glu Ser Leu Ser Val Gly Gly Thr Ser Val Thr Pro Arg
        755                 760                 765

Arg Ile Ser Trp Arg Gln Arg Ile Phe Leu Arg Val Ala Ser Pro Met
770                 775                 780

Asn Lys Ser Pro Ser Ala Met Gln Gln Gln Asp Gly Leu Asp Arg Asn
785                 790                 795                 800

Glu Leu Leu Pro Leu Ser Pro Leu Ser Pro Thr Met Glu Glu Glu Pro
            805                 810                 815

Leu Val Ile Phe Leu Ser Gly Glu Asp Asp Pro Glu Lys Ile Glu Glu
                820                 825                 830

Arg Lys Lys Ser Lys Glu Leu Arg Ser Leu Trp Arg Lys Ala Ile His
            835                 840                 845

Gln Gln Ile Leu Leu Leu Arg Met Glu Lys Glu Asn Gln Lys Leu Glu
        850                 855                 860

Gly Ala Ser Arg Asp Glu Leu Gln Ser Arg Lys Val Lys Leu Asp Tyr
865                 870                 875                 880

Glu Glu Val Gly Ala Cys Gln Lys Glu Val Leu Ile Thr Trp Asp Lys
                885                 890                 895

Lys Leu Leu Asn Cys Arg Ala Lys Ile Arg Cys Asp Met Glu Asp Ile
            900                 905                 910

His Thr Leu Leu Lys Glu Gly Val Pro Lys Ser Arg Arg Gly Glu Ile
            915                 920                 925

Trp Gln Phe Leu Ala Leu Gln Tyr Arg Leu Arg His Arg Leu Pro Asn
    930                 935                 940

Lys Gln Gln Pro Pro Asp Ile Ser Tyr Lys Glu Leu Leu Lys Gln Leu
945                 950                 955                 960

Thr Ala Gln Gln His Ala Ile Leu Val Asp Leu Gly Arg Thr Phe Pro
            965                 970                 975

Thr His Pro Tyr Phe Ser Val Gln Leu Gly Pro Gly Gln Leu Ser Leu
        980                 985                 990

Phe Asn Leu Leu Lys Ala Tyr Ser  Leu Leu Asp Lys Glu  Val Gly Tyr
            995                 1000                1005

Cys Gln  Gly Ile Ser Phe Val  Ala Gly Val Leu Leu  Leu His Met
    1010                1015                1020

Ser Glu  Glu Gln Ala Phe Glu  Met Leu Lys Phe Leu  Met Tyr Asp
    1025                1030                1035
```

```
Leu Gly Phe Arg Lys Gln Tyr Arg Pro Asp Met Met Ser Leu Gln
    1040                1045                1050

Ile Gln Met Tyr Gln Leu Ser Arg Leu Leu His Asp Tyr His Arg
    1055                1060                1065

Asp Leu Tyr Asn His Leu Glu Asn Glu Ile Ser Pro Ser Leu
    1070                1075                1080

Tyr Ala Ala Pro Trp Phe Leu Thr Leu Phe Ala Ser Gln Phe Ser
    1085                1090                1095

Leu Gly Phe Val Ala Arg Val Phe Asp Ile Ile Phe Leu Gln Gly
    1100                1105                1110

Thr Glu Val Ile Phe Lys Val Ala Leu Ser Leu Leu Ser Ser Gln
    1115                1120                1125

Glu Thr Leu Ile Met Glu Cys Glu Ser Phe Glu Asn Ile Val Glu
    1130                1135                1140

Phe Leu Lys Asn Thr Leu Pro Asp Met Asn Thr Ser Glu Met Glu
    1145                1150                1155

Lys Ile Ile Thr Gln Val Phe Glu Met Asp Ile Ser Lys Gln Leu
    1160                1165                1170

His Ala Tyr Glu Val Glu Tyr His Val Leu Gln Asp Glu Leu Gln
    1175                1180                1185

Glu Ser Ser Tyr Ser Cys Glu Asp Ser Glu Thr Leu Glu Lys Leu
    1190                1195                1200

Glu Arg Ala Asn Ser Gln Leu Lys Arg Gln Asn Met Asp Leu Leu
    1205                1210                1215

Glu Lys Leu Gln Val Ala His Thr Lys Ile Gln Ala Leu Glu Ser
    1220                1225                1230

Asn Leu Glu Asn Leu Leu Thr Arg Glu Thr Lys Met Lys Ser Leu
    1235                1240                1245

Ile Arg Thr Leu Glu Gln Glu Lys Met Ala Tyr Gln Lys Thr Val
    1250                1255                1260

Glu Gln Leu Arg Lys Leu Leu Pro Ala Asp Ala Leu Ala Asn Cys
    1265                1270                1275

Asp Leu Leu Leu Arg Asp Leu Asn Cys Asn Pro Asn Asn Lys Ala
    1280                1285                1290

Lys Ile Gly Asn Lys Pro
    1295

<210> SEQ ID NO 2
<211> LENGTH: 435
<212> TYPE: PRT
<213> ORGANISM: Homo sapiens

<400> SEQUENCE: 2

Gly Ala Ser Arg Asp Glu Leu Gln Ser Arg Lys Val Lys Leu Asp Tyr
1               5                   10                  15

Glu Glu Val Gly Ala Cys Gln Lys Glu Val Leu Ile Thr Trp Asp Lys
                20                  25                  30

Lys Leu Leu Asn Cys Arg Ala Lys Ile Arg Cys Asp Met Glu Asp Ile
            35                  40                  45

His Thr Leu Leu Lys Glu Gly Val Pro Lys Ser Arg Arg Gly Glu Ile
        50                  55                  60

Trp Gln Phe Leu Ala Leu Gln Tyr Arg Leu Arg His Arg Leu Pro Asn
65                  70                  75                  80

Lys Gln Gln Pro Pro Asp Ile Ser Tyr Lys Glu Leu Leu Lys Gln Leu
                85                  90                  95
```

```
Thr Ala Gln Gln His Ala Ile Leu Val Asp Leu Gly Arg Thr Phe Pro
            100                 105                 110

Thr His Pro Tyr Phe Ser Val Gln Leu Gly Pro Gly Gln Leu Ser Leu
            115                 120                 125

Phe Asn Leu Leu Lys Ala Tyr Ser Leu Leu Asp Lys Glu Val Gly Tyr
        130                 135                 140

Cys Gln Gly Ile Ser Phe Val Ala Gly Val Leu Leu His Met Ser
145                 150                 155                 160

Glu Glu Gln Ala Phe Glu Met Leu Lys Phe Leu Met Tyr Asp Leu Gly
                165                 170                 175

Phe Arg Lys Gln Tyr Arg Pro Asp Met Met Ser Leu Gln Ile Gln Met
            180                 185                 190

Tyr Gln Leu Ser Arg Leu Leu His Asp Tyr His Arg Asp Leu Tyr Asn
        195                 200                 205

His Leu Glu Glu Asn Glu Ile Ser Pro Ser Leu Tyr Ala Ala Pro Trp
210                 215                 220

Phe Leu Thr Leu Phe Ala Ser Gln Phe Ser Leu Gly Phe Val Ala Arg
225                 230                 235                 240

Val Phe Asp Ile Ile Phe Leu Gln Gly Thr Glu Val Ile Phe Lys Val
                245                 250                 255

Ala Leu Ser Leu Leu Ser Ser Gln Glu Thr Leu Ile Met Glu Cys Glu
            260                 265                 270

Ser Phe Glu Asn Ile Val Glu Phe Leu Lys Asn Thr Leu Pro Asp Met
        275                 280                 285

Asn Thr Ser Glu Met Glu Lys Ile Ile Thr Gln Val Phe Glu Met Asp
        290                 295                 300

Ile Ser Lys Gln Leu His Ala Tyr Glu Val Tyr His Val Leu Gln
305                 310                 315                 320

Asp Glu Leu Gln Glu Ser Ser Tyr Ser Cys Glu Asp Ser Glu Thr Leu
                325                 330                 335

Glu Lys Leu Glu Arg Ala Asn Ser Gln Leu Lys Arg Gln Asn Met Asp
            340                 345                 350

Leu Leu Glu Lys Leu Gln Val Ala His Thr Lys Ile Gln Ala Leu Glu
        355                 360                 365

Ser Asn Leu Glu Asn Leu Leu Thr Arg Glu Thr Lys Met Lys Ser Leu
370                 375                 380

Ile Arg Thr Leu Glu Gln Glu Lys Met Ala Tyr Gln Lys Thr Val Glu
385                 390                 395                 400

Gln Leu Arg Lys Leu Leu Pro Ala Asp Ala Leu Ala Asn Cys Asp Leu
                405                 410                 415

Leu Leu Arg Asp Leu Asn Cys Asn Pro Asn Asn Lys Ala Lys Ile Gly
            420                 425                 430

Asn Lys Pro
        435

<210> SEQ ID NO 3
<211> LENGTH: 212
<212> TYPE: PRT
<213> ORGANISM: Homo sapiens

<400> SEQUENCE: 3

Met Ala Tyr Ala Tyr Leu Phe Lys Tyr Ile Ile Ile Gly Asp Thr Gly
1               5                   10                  15

Val Gly Lys Ser Cys Leu Leu Leu Gln Phe Thr Asp Lys Arg Phe Gln
            20                  25                  30
```

```
Pro Val His Asp Leu Thr Ile Gly Val Glu Phe Gly Ala Arg Met Ile
            35                  40                  45

Thr Ile Asp Gly Lys Gln Ile Lys Leu Gln Ile Trp Asp Thr Ala Gly
    50                  55                  60

Gln Glu Ser Phe Arg Ser Ile Thr Arg Ser Tyr Tyr Arg Gly Ala Ala
65                  70                  75                  80

Gly Ala Leu Leu Val Tyr Asp Ile Thr Arg Arg Asp Thr Phe Asn His
                85                  90                  95

Leu Thr Thr Trp Leu Glu Asp Ala Arg Gln His Ser Asn Ser Asn Met
            100                 105                 110

Val Ile Met Leu Ile Gly Asn Lys Ser Asp Leu Glu Ser Arg Arg Glu
        115                 120                 125

Val Lys Lys Glu Glu Gly Glu Ala Phe Ala Arg Glu His Gly Leu Ile
    130                 135                 140

Phe Met Glu Thr Ser Ala Lys Thr Ala Ser Asn Val Glu Glu Ala Phe
145                 150                 155                 160

Ile Asn Thr Ala Lys Glu Ile Tyr Glu Lys Ile Gln Glu Gly Val Phe
                165                 170                 175

Asp Ile Asn Asn Glu Ala Asn Gly Ile Lys Ile Gly Pro Gln His Ala
            180                 185                 190

Ala Thr Asn Ala Thr His Ala Gly Asn Gln Gly Gly Gln Gln Ala Gly
        195                 200                 205

Gly Gly Cys Cys
    210

<210> SEQ ID NO 4
<211> LENGTH: 207
<212> TYPE: PRT
<213> ORGANISM: Homo sapiens

<400> SEQUENCE: 4

Met Ala Lys Thr Tyr Asp Tyr Leu Phe Lys Leu Leu Leu Ile Gly Asp
1               5                   10                  15

Ser Gly Val Gly Lys Thr Cys Val Leu Phe Arg Phe Ser Glu Asp Ala
            20                  25                  30

Phe Asn Ser Thr Phe Ile Ser Thr Ile Gly Ile Asp Phe Lys Ile Arg
        35                  40                  45

Thr Ile Glu Leu Asp Gly Lys Arg Ile Lys Leu Gln Ile Trp Asp Thr
    50                  55                  60

Ala Gly Gln Glu Arg Phe Arg Thr Ile Thr Thr Ala Tyr Tyr Arg Gly
65                  70                  75                  80

Ala Met Gly Ile Met Leu Val Tyr Asp Ile Thr Asn Glu Lys Ser Phe
                85                  90                  95

Asp Asn Ile Arg Asn Trp Ile Arg Asn Ile Glu Glu His Ala Ser Ala
            100                 105                 110

Asp Val Glu Lys Met Ile Leu Gly Asn Lys Cys Asp Val Asn Asp Lys
        115                 120                 125

Arg Gln Val Ser Lys Glu Arg Gly Glu Lys Leu Ala Leu Asp Tyr Gly
    130                 135                 140

Ile Lys Phe Met Glu Thr Ser Ala Lys Ala Asn Ile Asn Val Glu Asn
145                 150                 155                 160

Ala Phe Phe Thr Leu Ala Arg Asp Ile Lys Ala Lys Met Asp Lys Lys
                165                 170                 175
```

```
Leu Glu Gly Asn Ser Pro Gln Gly Ser Asn Gln Gly Val Lys Ile Thr
            180                 185                 190

Pro Asp Gln Gln Lys Arg Ser Ser Phe Phe Arg Cys Val Leu Leu
        195                 200                 205
```

<210> SEQ ID NO 5
<211> LENGTH: 207
<212> TYPE: PRT
<213> ORGANISM: Homo sapiens

<400> SEQUENCE: 5

```
Met Ala Lys Thr Tyr Asp Tyr Leu Phe Lys Leu Leu Leu Ile Gly Asp
1               5                   10                  15

Ser Gly Val Gly Lys Thr Cys Leu Leu Phe Arg Phe Ser Glu Asp Ala
            20                  25                  30

Phe Asn Thr Thr Phe Ile Ser Thr Ile Gly Ile Asp Phe Lys Ile Arg
        35                  40                  45

Thr Ile Glu Leu Asp Gly Lys Lys Ile Lys Leu Gln Ile Trp Asp Thr
    50                  55                  60

Ala Gly Gln Glu Arg Phe Arg Thr Ile Thr Thr Ala Tyr Tyr Arg Gly
65                  70                  75                  80

Ala Met Gly Ile Met Leu Val Tyr Asp Ile Thr Asn Glu Lys Ser Phe
                85                  90                  95

Asp Asn Ile Lys Asn Trp Ile Arg Asn Ile Glu Glu His Ala Ser Ser
            100                 105                 110

Asp Val Glu Arg Met Ile Leu Gly Asn Lys Cys Asp Met Asn Asp Lys
        115                 120                 125

Arg Gln Val Ser Lys Glu Arg Gly Glu Lys Leu Ala Ile Asp Tyr Gly
    130                 135                 140

Ile Lys Phe Leu Glu Thr Ser Ala Lys Ser Ser Ala Asn Val Glu Glu
145                 150                 155                 160

Ala Phe Phe Thr Leu Ala Arg Asp Ile Met Thr Lys Leu Asn Arg Lys
                165                 170                 175

Met Asn Asp Ser Asn Ser Ala Gly Ala Gly Gly Pro Val Lys Ile Thr
            180                 185                 190

Glu Asn Arg Ser Lys Lys Thr Ser Phe Phe Arg Cys Ser Leu Leu
        195                 200                 205
```

<210> SEQ ID NO 6
<211> LENGTH: 200
<212> TYPE: PRT
<213> ORGANISM: Homo sapiens

<400> SEQUENCE: 6

```
Met Ala Lys Lys Thr Tyr Asp Leu Leu Phe Lys Leu Leu Leu Ile Gly
1               5                   10                  15

Asp Ser Gly Val Gly Lys Thr Cys Val Leu Phe Arg Phe Ser Asp Asp
            20                  25                  30

Ala Phe Asn Thr Thr Phe Ile Ser Thr Ile Gly Ile Asp Phe Lys Ile
        35                  40                  45

Lys Thr Val Glu Leu Gln Gly Lys Ile Lys Leu Gln Ile Trp Asp
    50                  55                  60

Thr Ala Gly Gln Glu Arg Phe His Thr Ile Thr Thr Ser Tyr Tyr Arg
65                  70                  75                  80

Gly Ala Met Gly Ile Met Leu Val Tyr Asp Ile Thr Asn Gly Lys Ser
                85                  90                  95
```

```
Phe Glu Asn Ile Ser Lys Trp Leu Arg Asn Ile Asp Glu His Ala Asn
            100                 105                 110

Glu Asp Val Glu Arg Met Leu Leu Gly Asn Lys Cys Asp Met Asp Asp
        115                 120                 125

Lys Arg Val Val Pro Lys Gly Gly Gln Ile Ala Arg Glu His
    130                 135                 140

Gly Ile Arg Phe Phe Glu Thr Ser Ala Lys Ala Asn Ile Asn Ile Glu
145                 150                 155                 160

Lys Ala Phe Leu Thr Leu Ala Glu Asp Ile Leu Arg Lys Thr Pro Val
                165                 170                 175

Lys Glu Pro Asn Ser Glu Asn Val Asp Ile Ser Ser Gly Gly Gly Val
                180                 185                 190

Thr Gly Trp Lys Ser Lys Cys Cys
            195                 200

<210> SEQ ID NO 7
<211> LENGTH: 215
<212> TYPE: PRT
<213> ORGANISM: Homo sapiens

<400> SEQUENCE: 7

Met Ala Thr Ala Pro Tyr Asn Tyr Ser Tyr Ile Phe Lys Tyr Ile Ile
1               5                   10                  15

Ile Gly Asp Met Gly Val Gly Lys Ser Cys Leu Leu His Gln Phe Thr
                20                  25                  30

Glu Lys Lys Phe Met Ala Asp Cys Pro His Thr Ile Gly Val Glu Phe
            35                  40                  45

Gly Thr Arg Ile Ile Glu Val Ser Gly Gln Lys Ile Lys Leu Gln Ile
        50                  55                  60

Trp Asp Thr Ala Gly Gln Glu Arg Phe Arg Ala Val Thr Arg Ser Tyr
65                  70                  75                  80

Tyr Arg Gly Ala Ala Gly Ala Leu Met Val Tyr Asp Ile Thr Arg Arg
                85                  90                  95

Ser Thr Tyr Asn His Leu Ser Ser Trp Leu Thr Asp Ala Arg Asn Leu
            100                 105                 110

Thr Asn Pro Asn Thr Val Ile Ile Leu Ile Gly Asn Lys Ala Asp Leu
        115                 120                 125

Glu Ala Gln Arg Asp Val Thr Tyr Glu Glu Ala Lys Gln Phe Ala Glu
    130                 135                 140

Glu Asn Gly Leu Leu Phe Leu Glu Ala Ser Ala Lys Thr Gly Glu Asn
145                 150                 155                 160

Val Glu Asp Ala Phe Leu Glu Ala Ala Lys Lys Ile Tyr Gln Asn Ile
                165                 170                 175

Gln Asp Gly Ser Leu Asp Leu Asn Ala Ala Glu Ser Gly Val Gln His
            180                 185                 190

Lys Pro Ser Ala Pro Gln Gly Gly Arg Leu Thr Ser Glu Pro Gln Pro
        195                 200                 205

Gln Arg Glu Gly Cys Gly Cys
    210                 215

<210> SEQ ID NO 8
<211> LENGTH: 201
<212> TYPE: PRT
<213> ORGANISM: Artificial Sequence
<220> FEATURE:
<223> OTHER INFORMATION: Consensus Sequence for Selected Human Rab
      Proteins
```

```
<220> FEATURE:
<221> NAME/KEY: MISC_FEATURE
<222> LOCATION: (1)..(2)
<223> OTHER INFORMATION: Xaa denotes any amino acid residue.
<220> FEATURE:
<221> NAME/KEY: MISC_FEATURE
<222> LOCATION: (4)..(4)
<223> OTHER INFORMATION: Xaa denotes any amino acid residue.
<220> FEATURE:
<221> NAME/KEY: MISC_FEATURE
<222> LOCATION: (15)..(15)
<223> OTHER INFORMATION: Xaa denotes any amino acid residue.
<220> FEATURE:
<221> NAME/KEY: MISC_FEATURE
<222> LOCATION: (24)..(24)
<223> OTHER INFORMATION: Xaa denotes any amino acid residue.
<220> FEATURE:
<221> NAME/KEY: MISC_FEATURE
<222> LOCATION: (28)..(28)
<223> OTHER INFORMATION: Xaa denotes Asn, Asp, Gln, or Glu.
<220> FEATURE:
<221> NAME/KEY: MISC_FEATURE
<222> LOCATION: (30)..(30)
<223> OTHER INFORMATION: Xaa denotes any amino acid residue.
<220> FEATURE:
<221> NAME/KEY: MISC_FEATURE
<222> LOCATION: (32)..(37)
<223> OTHER INFORMATION: Xaa denotes any amino acid residue.
<220> FEATURE:
<221> NAME/KEY: MISC_FEATURE
<222> LOCATION: (41)..(41)
<223> OTHER INFORMATION: Xaa denotes Ile or Val.
<220> FEATURE:
<221> NAME/KEY: MISC_FEATURE
<222> LOCATION: (42)..(42)
<223> OTHER INFORMATION: Xaa denotes Asn, Asp, Gln, or Glu.
<220> FEATURE:
<221> NAME/KEY: MISC_FEATURE
<222> LOCATION: (45)..(45)
<223> OTHER INFORMATION: Xaa denotes any amino acid residue.
<220> FEATURE:
<221> NAME/KEY: MISC_FEATURE
<222> LOCATION: (47)..(47)
<223> OTHER INFORMATION: Xaa denotes any amino acid residue.
<220> FEATURE:
<221> NAME/KEY: MISC_FEATURE
<222> LOCATION: (48)..(48)
<223> OTHER INFORMATION: Xaa denotes Ile or Val.
<220> FEATURE:
<221> NAME/KEY: MISC_FEATURE
<222> LOCATION: (50)..(50)
<223> OTHER INFORMATION: Xaa denotes any amino acid residue.
<220> FEATURE:
<221> NAME/KEY: MISC_FEATURE
<222> LOCATION: (70)..(70)
<223> OTHER INFORMATION: Xaa denotes any amino acid residue.
<220> FEATURE:
<221> NAME/KEY: MISC_FEATURE
<222> LOCATION: (71)..(71)
<223> OTHER INFORMATION: Xaa denotes Ile or Val.
<220> FEATURE:
<221> NAME/KEY: MISC_FEATURE
<222> LOCATION: (83)..(84)
<223> OTHER INFORMATION: Xaa denotes Leu or Met.
<220> FEATURE:
<221> NAME/KEY: MISC_FEATURE
<222> LOCATION: (92)..(92)
<223> OTHER INFORMATION: Xaa denotes any amino acid residue.
<220> FEATURE:
<221> NAME/KEY: MISC_FEATURE
<222> LOCATION: (94)..(94)
<223> OTHER INFORMATION: Xaa denotes Phe or Tyr.
<220> FEATURE:
<221> NAME/KEY: MISC_FEATURE
<222> LOCATION: (95)..(95)
<223> OTHER INFORMATION: Xaa denotes Asn, Asp, Gln, or Glu.
```

-continued

```
<220> FEATURE:
<221> NAME/KEY: MISC_FEATURE
<222> LOCATION: (98)..(99)
<223> OTHER INFORMATION: Xaa denotes any amino acid residue.
<220> FEATURE:
<221> NAME/KEY: MISC_FEATURE
<222> LOCATION: (102)..(102)
<223> OTHER INFORMATION: Xaa denotes any amino acid residue.
<220> FEATURE:
<221> NAME/KEY: MISC_FEATURE
<222> LOCATION: (103)..(103)
<223> OTHER INFORMATION: Xaa denotes Asn, Asp, Gln, or Glu.
<220> FEATURE:
<221> NAME/KEY: MISC_FEATURE
<222> LOCATION: (106)..(106)
<223> OTHER INFORMATION: Xaa denotes Asn, Asp, Gln, or Glu.
<220> FEATURE:
<221> NAME/KEY: MISC_FEATURE
<222> LOCATION: (108)..(108)
<223> OTHER INFORMATION: Xaa denotes any amino acid residue.
<220> FEATURE:
<221> NAME/KEY: MISC_FEATURE
<222> LOCATION: (110)..(110)
<223> OTHER INFORMATION: Xaa denotes any amino acid residue.
<220> FEATURE:
<221> NAME/KEY: MISC_FEATURE
<222> LOCATION: (111)..(111)
<223> OTHER INFORMATION: Xaa denotes Asn, Asp, Gln, or Glu.
<220> FEATURE:
<221> NAME/KEY: MISC_FEATURE
<222> LOCATION: (112)..(112)
<223> OTHER INFORMATION: Xaa denotes any amino acid residue.
<220> FEATURE:
<221> NAME/KEY: MISC_FEATURE
<222> LOCATION: (121)..(121)
<223> OTHER INFORMATION: Xaa denotes any amino acid residue.
<220> FEATURE:
<221> NAME/KEY: MISC_FEATURE
<222> LOCATION: (124)..(124)
<223> OTHER INFORMATION: Xaa denotes Asn, Asp, Gln, or Glu.
<220> FEATURE:
<221> NAME/KEY: MISC_FEATURE
<222> LOCATION: (125)..(126)
<223> OTHER INFORMATION: Xaa denotes any amino acid residue.
<220> FEATURE:
<221> NAME/KEY: MISC_FEATURE
<222> LOCATION: (128)..(128)
<223> OTHER INFORMATION: Xaa denotes any amino acid residue.
<220> FEATURE:
<221> NAME/KEY: MISC_FEATURE
<222> LOCATION: (130)..(130)
<223> OTHER INFORMATION: Xaa denotes any amino acid residue.
<220> FEATURE:
<221> NAME/KEY: MISC_FEATURE
<222> LOCATION: (136)..(136)
<223> OTHER INFORMATION: Xaa denotes any amino acid residue.
<220> FEATURE:
<221> NAME/KEY: MISC_FEATURE
<222> LOCATION: (139)..(139)
<223> OTHER INFORMATION: Xaa denotes any amino acid residue.
<220> FEATURE:
<221> NAME/KEY: MISC_FEATURE
<222> LOCATION: (140)..(140)
<223> OTHER INFORMATION: Xaa denotes Asn, Asp, Gln, or Glu.
<220> FEATURE:
<221> NAME/KEY: MISC_FEATURE
<222> LOCATION: (141)..(141)
<223> OTHER INFORMATION: Xaa denotes any amino acid residue.
<220> FEATURE:
<221> NAME/KEY: MISC_FEATURE
<222> LOCATION: (144)..(144)
<223> OTHER INFORMATION: Xaa denotes any amino acid residue.
<220> FEATURE:
<221> NAME/KEY: MISC_FEATURE
<222> LOCATION: (146)..(146)
<223> OTHER INFORMATION: Xaa denotes any amino acid residue.
```

```
<220> FEATURE:
<221> NAME/KEY: MISC_FEATURE
<222> LOCATION: (153)..(154)
<223> OTHER INFORMATION: Xaa denotes any amino acid residue.
<220> FEATURE:
<221> NAME/KEY: MISC_FEATURE
<222> LOCATION: (156)..(156)
<223> OTHER INFORMATION: Xaa denotes Ile or Val.
<220> FEATURE:
<221> NAME/KEY: MISC_FEATURE
<222> LOCATION: (158)..(158)
<223> OTHER INFORMATION: Xaa denotes any amino acid residue.
<220> FEATURE:
<221> NAME/KEY: MISC_FEATURE
<222> LOCATION: (161)..(163)
<223> OTHER INFORMATION: Xaa denotes any amino acid residue.
<220> FEATURE:
<221> NAME/KEY: MISC_FEATURE
<222> LOCATION: (166)..(166)
<223> OTHER INFORMATION: Xaa denotes any amino acid residue.
<220> FEATURE:
<221> NAME/KEY: MISC_FEATURE
<222> LOCATION: (169)..(169)
<223> OTHER INFORMATION: Xaa denotes any amino acid residue.
<220> FEATURE:
<221> NAME/KEY: MISC_FEATURE
<222> LOCATION: (173)..(173)
<223> OTHER INFORMATION: Xaa denotes any amino acid residue.
<220> FEATURE:
<221> NAME/KEY: MISC_FEATURE
<222> LOCATION: (175)..(176)
<223> OTHER INFORMATION: Xaa denotes any amino acid residue.
<220> FEATURE:
<221> NAME/KEY: MISC_FEATURE
<222> LOCATION: (178)..(178)
<223> OTHER INFORMATION: Xaa denotes any amino acid residue.
<220> FEATURE:
<221> NAME/KEY: MISC_FEATURE
<222> LOCATION: (180)..(183)
<223> OTHER INFORMATION: Xaa denotes any amino acid residue.
<220> FEATURE:
<221> NAME/KEY: MISC_FEATURE
<222> LOCATION: (185)..(187)
<223> OTHER INFORMATION: Xaa denotes any amino acid residue.
<220> FEATURE:
<221> NAME/KEY: MISC_FEATURE
<222> LOCATION: (190)..(191)
<223> OTHER INFORMATION: Xaa denotes any amino acid residue.
<220> FEATURE:
<221> NAME/KEY: MISC_FEATURE
<222> LOCATION: (193)..(197)
<223> OTHER INFORMATION: Xaa denotes any amino acid residue.

<400> SEQUENCE: 8

Xaa Xaa Tyr Xaa Tyr Leu Phe Lys Tyr Ile Ile Ile Gly Asp Xaa Gly
1               5                   10                  15

Val Gly Lys Ser Cys Leu Leu Xaa Gln Phe Thr Xaa Lys Xaa Phe Xaa
                20                  25                  30

Xaa Xaa Xaa Xaa Xaa Thr Ile Gly Xaa Xaa Phe Gly Xaa Arg Xaa Xaa
            35                  40                  45

Glu Xaa Asp Gly Lys Lys Ile Lys Leu Gln Ile Trp Asp Thr Ala Gly
50                  55                  60

Gln Glu Arg Phe Arg Xaa Xaa Thr Arg Ser Tyr Tyr Arg Gly Ala Ala
65                  70                  75                  80

Gly Ala Xaa Xaa Val Tyr Asp Ile Thr Arg Arg Xaa Thr Xaa Xaa His
                85                  90                  95

Leu Xaa Xaa Trp Leu Xaa Xaa Ala Arg Xaa His Xaa Asn Xaa Xaa Xaa
            100                 105                 110

Val Ile Met Leu Ile Gly Asn Lys Xaa Asp Leu Xaa Xaa Xaa Arg Xaa
            115                 120                 125
```

```
Val Xaa Lys Glu Glu Gly Glu Xaa Phe Ala Xaa Xaa Xaa Gly Leu Xaa
    130                 135                 140

Phe Xaa Glu Thr Ser Ala Lys Thr Xaa Xaa Asn Xaa Glu Xaa Ala Phe
145                 150                 155                 160

Xaa Xaa Xaa Ala Lys Xaa Ile Tyr Xaa Lys Ile Gln Xaa Gly Xaa Xaa
                165                 170                 175

Asp Xaa Asn Xaa Xaa Xaa Gly Xaa Xaa Lys Pro Xaa Xaa Ala
        180                 185                 190

Xaa Xaa Xaa Xaa Xaa Gln Gly Gly Cys
        195                 200
```

```
<210> SEQ ID NO 9
<211> LENGTH: 12
<212> TYPE: PRT
<213> ORGANISM: Homo sapiens

<400> SEQUENCE: 9

Leu Val Asp Leu Gly Arg Thr Phe Pro Thr His Pro
1               5                   10
```

```
<210> SEQ ID NO 10
<211> LENGTH: 218
<212> TYPE: PRT
<213> ORGANISM: Homo sapiens

<400> SEQUENCE: 10

Met Thr Asp Gly Asp Tyr Asp Tyr Leu Ile Lys Leu Leu Ala Leu Gly
1               5                   10                  15

Asp Ser Gly Val Gly Lys Thr Thr Phe Leu Tyr Arg Tyr Thr Asp Asn
                20                  25                  30

Lys Phe Asn Pro Lys Phe Ile Thr Thr Val Gly Ile Asp Phe Arg Glu
            35                  40                  45

Lys Arg Val Val Tyr Asn Ala Gln Gly Pro Asn Gly Ser Ser Gly Lys
        50                  55                  60

Ala Phe Lys Val His Leu Gln Leu Trp Asp Thr Ala Gly Gln Glu Arg
65                  70                  75                  80

Phe Arg Ser Leu Thr Thr Ala Phe Phe Arg Asp Ala Met Gly Phe Leu
                85                  90                  95

Leu Met Phe Asp Leu Thr Ser Gln Gln Ser Phe Leu Asn Val Arg Asn
            100                 105                 110

Trp Met Ser Gln Leu Gln Ala Asn Ala Tyr Cys Glu Asn Pro Asp Ile
        115                 120                 125

Val Leu Ile Gly Asn Lys Ala Asp Leu Pro Asp Gln Arg Glu Val Asn
    130                 135                 140

Glu Arg Gln Ala Arg Glu Leu Ala Asp Lys Tyr Gly Ile Pro Tyr Phe
145                 150                 155                 160

Glu Thr Ser Ala Ala Thr Gly Gln Asn Val Glu Lys Ala Val Glu Thr
                165                 170                 175

Leu Leu Asp Leu Ile Met Lys Arg Met Glu Gln Cys Val Glu Lys Thr
            180                 185                 190

Gln Ile Pro Asp Thr Val Asn Gly Gly Asn Ser Gly Asn Leu Asp Gly
        195                 200                 205

Glu Lys Pro Pro Glu Lys Lys Cys Ile Cys
    210                 215
```

<210> SEQ ID NO 11
<211> LENGTH: 218
<212> TYPE: PRT
<213> ORGANISM: Homo sapiens

<400> SEQUENCE: 11

Met Ser Gln Thr Ala Met Ser Glu Thr Tyr Asp Phe Leu Phe Lys Phe
1               5                   10                  15

Leu Val Ile Gly Asn Ala Gly Thr Gly Lys Ser Cys Leu Leu His Gln
            20                  25                  30

Phe Ile Glu Lys Lys Phe Lys Asp Asp Ser Asn His Thr Ile Gly Val
        35                  40                  45

Glu Phe Gly Ser Lys Ile Ile Asn Val Gly Gly Lys Tyr Val Lys Leu
    50                  55                  60

Gln Ile Trp Asp Thr Ala Gly Gln Glu Arg Phe Arg Ser Val Thr Arg
65                  70                  75                  80

Ser Tyr Tyr Arg Gly Ala Ala Gly Ala Leu Leu Val Tyr Asp Ile Thr
                85                  90                  95

Ser Arg Glu Thr Tyr Asn Ala Leu Thr Asn Trp Leu Thr Asp Ala Arg
            100                 105                 110

Met Leu Ala Ser Gln Asn Ile Val Ile Ile Leu Cys Gly Asn Lys Lys
        115                 120                 125

Asp Leu Asp Ala Asp Arg Glu Val Thr Phe Leu Glu Ala Ser Arg Phe
    130                 135                 140

Ala Gln Glu Asn Glu Leu Met Phe Leu Glu Thr Ser Ala Leu Thr Gly
145                 150                 155                 160

Glu Asn Val Glu Glu Ala Phe Val Gln Cys Ala Arg Lys Ile Leu Asn
                165                 170                 175

Lys Ile Glu Ser Gly Glu Leu Asp Pro Glu Arg Met Gly Ser Gly Ile
            180                 185                 190

Gln Tyr Gly Asp Ala Ala Leu Arg Gln Leu Arg Ser Pro Arg Arg Ala
        195                 200                 205

Gln Ala Pro Asn Ala Gln Glu Cys Gly Cys
    210                 215

<210> SEQ ID NO 12
<211> LENGTH: 216
<212> TYPE: PRT
<213> ORGANISM: Homo sapiens

<400> SEQUENCE: 12

Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

```
Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
    130                 135                 140

Lys Asn Gly Leu Ser Phe Ile Glu Thr Ser Ala Leu Asp Ser Thr Asn
145                 150                 155                 160

Val Glu Ala Ala Phe Gln Thr Ile Leu Thr Glu Ile Tyr Arg Ile Val
                165                 170                 175

Ser Gln Lys Gln Met Ser Asp Arg Arg Glu Asn Asp Met Ser Pro Ser
            180                 185                 190

Asn Asn Val Val Pro Ile His Val Pro Pro Thr Thr Glu Asn Lys Pro
        195                 200                 205

Lys Val Gln Cys Cys Gln Asn Ile
    210                 215
```

<210> SEQ ID NO 13
<211> LENGTH: 225
<212> TYPE: PRT
<213> ORGANISM: Homo sapiens

<400> SEQUENCE: 13

```
Met Ala Ala Ala Gly Gly Gly Gly Gly Ala Ala Ala Ala Ala Gly Arg
1               5                   10                  15

Ala Tyr Ser Phe Lys Val Val Leu Leu Gly Glu Gly Cys Val Gly Lys
            20                  25                  30

Thr Ser Leu Val Leu Arg Tyr Cys Glu Asn Lys Phe Asn Asp Lys His
        35                  40                  45

Ile Thr Thr Leu Gln Ala Ser Phe Leu Thr Lys Lys Leu Asn Ile Gly
    50                  55                  60

Gly Lys Arg Val Asn Leu Ala Ile Trp Asp Thr Ala Gly Gln Glu Arg
65                  70                  75                  80

Phe His Ala Leu Gly Pro Ile Tyr Tyr Arg Asp Ser Asn Gly Ala Ile
                85                  90                  95

Leu Val Tyr Asp Ile Thr Asp Glu Asp Ser Phe Gln Lys Val Lys Asn
            100                 105                 110

Trp Val Lys Glu Leu Arg Lys Met Leu Gly Asn Glu Ile Cys Leu Cys
        115                 120                 125

Ile Val Gly Asn Lys Ile Asp Leu Glu Lys Glu Arg His Val Ser Ile
    130                 135                 140

Gln Glu Ala Glu Ser Tyr Ala Glu Ser Val Gly Ala Lys His Tyr His
145                 150                 155                 160

Thr Ser Ala Lys Gln Asn Lys Gly Ile Glu Glu Leu Phe Leu Asp Leu
                165                 170                 175

Cys Lys Arg Met Ile Glu Thr Ala Gln Val Asp Glu Arg Ala Lys Gly
            180                 185                 190

Asn Gly Ser Ser Gln Pro Gly Thr Ala Arg Arg Gly Val Gln Ile Ile
        195                 200                 205

Asp Asp Glu Pro Gln Ala Gln Thr Ser Gly Gly Cys Cys Ser Ser
    210                 215                 220

Gly
225
```

<210> SEQ ID NO 14
<211> LENGTH: 213
<212> TYPE: PRT
<213> ORGANISM: Homo sapiens

<400> SEQUENCE: 14

```
Met Ala Glu Asp Arg His Phe Leu Phe Lys Phe Leu Val Ile Gly Ser
1               5                   10                  15

Ala Gly Thr Gly Lys Ser Cys Leu Leu His Gln Phe Ile Glu Asn Lys
            20                  25                  30

Phe Lys Gln Asp Ser Asn His Thr Ile Gly Val Glu Phe Gly Ser Arg
        35                  40                  45

Val Val Asn Val Gly Gly Lys Thr Val Lys Leu Gln Ile Trp Asp Thr
    50                  55                  60

Ala Gly Gln Glu Arg Phe Arg Ser Val Thr Arg Ser Tyr Tyr Arg Gly
65                  70                  75                  80

Ala Ala Gly Ala Leu Leu Val Tyr Asp Ile Thr Ser Arg Glu Thr Tyr
                85                  90                  95

Asn Ser Leu Ala Ala Trp Leu Thr Asp Ala Arg Thr Leu Ala Ser Pro
            100                 105                 110

Asn Ile Val Val Ile Leu Cys Gly Asn Lys Lys Asp Leu Asp Pro Glu
        115                 120                 125

Arg Glu Val Thr Phe Leu Glu Ala Ser Arg Phe Ala Gln Glu Asn Glu
130                 135                 140

Leu Met Phe Leu Glu Thr Ser Ala Leu Thr Gly Glu Asn Val Glu Glu
145                 150                 155                 160

Ala Phe Leu Lys Cys Ala Arg Thr Ile Leu Asn Lys Ile Asp Ser Gly
                165                 170                 175

Glu Leu Asp Pro Glu Arg Met Gly Ser Gly Ile Gln Tyr Gly Asp Ala
            180                 185                 190

Ser Leu Arg Gln Leu Arg Gln Pro Arg Ser Ala Gln Ala Val Ala Pro
        195                 200                 205

Gln Pro Cys Gly Cys
        210
```

<210> SEQ ID NO 15
<211> LENGTH: 218
<212> TYPE: PRT
<213> ORGANISM: Homo sapiens

<400> SEQUENCE: 15

```
Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
130                 135                 140
```

```
Lys Asn Asn Leu Ser Phe Ile Glu Thr Ser Ala Leu Asp Ser Thr Asn
145                 150                 155                 160

Val Glu Glu Ala Phe Lys Asn Ile Leu Thr Glu Ile Tyr Arg Ile Val
                165                 170                 175

Ser Gln Lys Gln Ile Ala Asp Cys Ala Ala His Asp Glu Ser Pro Gly
            180                 185                 190

Asn Asn Val Val Asp Ile Ser Val Pro Pro Thr Thr Asp Gly Gln Lys
        195                 200                 205

Pro Asn Lys Leu Gln Cys Cys Gln Asn Leu
    210                 215
```

<210> SEQ ID NO 16
<211> LENGTH: 205
<212> TYPE: PRT
<213> ORGANISM: Homo sapiens

<400> SEQUENCE: 16

```
Met Ser Ser Met Asn Pro Glu Tyr Asp Tyr Leu Phe Lys Leu Leu Leu
1               5                   10                  15

Ile Gly Asp Ser Gly Val Gly Lys Ser Cys Leu Leu Leu Arg Phe Ala
            20                  25                  30

Asp Asp Thr Tyr Thr Glu Ser Tyr Ile Ser Thr Ile Gly Val Asp Phe
        35                  40                  45

Lys Ile Arg Thr Ile Glu Leu Asp Gly Lys Thr Ile Lys Leu Gln Ile
    50                  55                  60

Trp Asp Thr Ala Gly Gln Glu Arg Phe Arg Thr Ile Thr Ser Ser Tyr
65                  70                  75                  80

Tyr Arg Gly Ala His Gly Ile Ile Val Val Tyr Asp Val Thr Asp Gln
                85                  90                  95

Glu Ser Phe Asn Asn Val Lys Gln Trp Leu Gln Glu Ile Asp Arg Tyr
            100                 105                 110

Ala Ser Glu Asn Val Asn Lys Leu Leu Val Gly Asn Lys Cys Asp Leu
        115                 120                 125

Thr Thr Lys Lys Val Val Asp Tyr Thr Thr Ala Lys Glu Phe Ala Asp
    130                 135                 140

Ser Leu Gly Ile Pro Phe Leu Glu Thr Ser Ala Lys Asn Ala Thr Asn
145                 150                 155                 160

Val Glu Gln Ser Phe Met Thr Met Ala Ala Glu Ile Lys Lys Arg Met
                165                 170                 175

Gly Pro Gly Ala Thr Ala Gly Gly Ala Glu Lys Ser Asn Val Lys Ile
            180                 185                 190

Gln Ser Thr Pro Val Lys Gln Ser Gly Gly Cys Cys
        195                 200                 205
```

<210> SEQ ID NO 17
<211> LENGTH: 201
<212> TYPE: PRT
<213> ORGANISM: Homo sapiens

<400> SEQUENCE: 17

```
Met Asn Pro Glu Tyr Asp Tyr Leu Phe Lys Leu Leu Leu Ile Gly Asp
1               5                   10                  15

Ser Gly Val Gly Lys Ser Cys Leu Leu Leu Arg Phe Ala Asp Asp Thr
            20                  25                  30

Tyr Thr Glu Asn Tyr Ile Ser Thr Ile Gly Val Asp Phe Lys Ile Arg
        35                  40                  45
```

```
Thr Ile Glu Leu Asp Gly Lys Thr Ile Lys Leu Gln Ile Trp Asp Thr
    50                  55                  60

Ala Gly Gln Glu Arg Phe Arg Thr Ile Thr Ser Ser Tyr Tyr Arg Gly
 65                  70                  75                  80

Ala His Gly Ile Ile Val Val Tyr Asp Val Thr Asp Gln Glu Ser Tyr
                 85                  90                  95

Ala Asn Val Lys Gln Trp Leu Gln Glu Ile Asp Arg Tyr Ala Ser Glu
            100                 105                 110

Asn Val Asn Lys Leu Leu Val Gly Asn Lys Ser Asp Leu Thr Thr Lys
            115                 120                 125

Lys Val Val Asp Asn Thr Thr Ala Lys Glu Phe Ala Asp Ser Leu Gly
130                 135                 140

Ile Pro Phe Leu Glu Thr Ser Ala Lys Asn Ala Thr Asn Val Glu Gln
145                 150                 155                 160

Ala Phe Met Thr Met Ala Ala Glu Ile Lys Lys Arg Met Gly Pro Gly
                165                 170                 175

Ala Ala Ser Gly Gly Glu Arg Pro Asn Leu Lys Ile Asp Ser Thr Pro
            180                 185                 190

Val Lys Pro Ala Gly Gly Gly Cys Cys
            195                 200

<210> SEQ ID NO 18
<211> LENGTH: 221
<212> TYPE: PRT
<213> ORGANISM: Homo sapiens

<400> SEQUENCE: 18

Met Ser Asp Gly Asp Tyr Asp Tyr Leu Ile Lys Phe Leu Ala Leu Gly
  1               5                  10                  15

Asp Ser Gly Val Gly Lys Thr Ser Val Leu Tyr Gln Tyr Thr Asp Gly
                 20                  25                  30

Lys Phe Asn Ser Lys Phe Ile Thr Thr Val Gly Ile Asp Phe Arg Glu
             35                  40                  45

Lys Arg Val Val Tyr Arg Ala Ser Gly Pro Asp Gly Ala Thr Gly Arg
 50                  55                  60

Gly Gln Arg Ile His Leu Gln Leu Trp Asp Thr Ala Gly Gln Glu Arg
 65                  70                  75                  80

Phe Arg Ser Leu Thr Thr Thr Phe Phe Arg Asp Ala Met Gly Phe Leu
                 85                  90                  95

Leu Leu Phe Asp Leu Thr Asn Glu Gln Ser Phe Leu Asn Val Arg Asn
            100                 105                 110

Trp Ile Ser Gln Leu Gln Met His Ala Tyr Cys Glu Asn Pro Asp Ile
            115                 120                 125

Val Leu Cys Gly Asn Lys Ser Asp Leu Glu Asp Gln Arg Val Val Lys
130                 135                 140

Glu Glu Glu Ala Ile Ala Leu Ala Glu Lys Tyr Gly Ile Pro Tyr Phe
145                 150                 155                 160

Glu Thr Ser Ala Ala Asn Gly Thr Asn Ile Ser Gln Ala Ile Glu Met
                165                 170                 175

Leu Leu Asp Leu Ile Met Lys Arg Met Glu Arg Cys Val Asp Lys Ser
            180                 185                 190

Trp Ile Pro Glu Gly Val Val Arg Ser Asn Gly His Ala Ser Thr Asp
            195                 200                 205

Gln Leu Ser Glu Glu Lys Glu Lys Gly Ala Cys Gly Cys
210                 215                 220
```

<210> SEQ ID NO 19
<211> LENGTH: 201
<212> TYPE: PRT
<213> ORGANISM: Homo sapiens

<400> SEQUENCE: 19

Met Ala Arg Asp Tyr Asp His Leu Phe Lys Leu Leu Ile Ile Gly Asp
1               5                   10                  15

Ser Gly Val Gly Lys Ser Ser Leu Leu Leu Arg Phe Ala Asp Asn Thr
            20                  25                  30

Phe Ser Gly Ser Tyr Ile Thr Thr Ile Gly Val Asp Phe Lys Ile Arg
        35                  40                  45

Thr Val Glu Ile Asn Gly Glu Lys Val Lys Leu Gln Ile Trp Asp Thr
    50                  55                  60

Ala Gly Gln Glu Arg Phe Arg Thr Ile Thr Ser Thr Tyr Tyr Arg Gly
65                  70                  75                  80

Thr His Gly Val Ile Val Val Tyr Asp Val Thr Ser Ala Glu Ser Phe
                85                  90                  95

Val Asn Val Lys Arg Trp Leu His Glu Ile Asn Gln Asn Cys Asp Asp
            100                 105                 110

Val Cys Arg Ile Leu Val Gly Asn Lys Asn Asp Asp Pro Glu Arg Lys
        115                 120                 125

Val Val Glu Thr Glu Asp Ala Tyr Lys Phe Ala Gly Gln Met Gly Ile
    130                 135                 140

Gln Leu Phe Glu Thr Ser Ala Lys Glu Asn Val Asn Val Glu Glu Met
145                 150                 155                 160

Phe Asn Cys Ile Thr Glu Leu Val Leu Arg Ala Lys Lys Asp Asn Leu
                165                 170                 175

Ala Lys Gln Gln Gln Gln Gln Asn Asp Val Val Lys Leu Thr Lys
            180                 185                 190

Asn Ser Lys Arg Lys Arg Cys Cys
            195                 200

<210> SEQ ID NO 20
<211> LENGTH: 220
<212> TYPE: PRT
<213> ORGANISM: Homo sapiens

<400> SEQUENCE: 20

Met Ala Ser Ala Thr Asp Ser Arg Tyr Gly Gln Lys Glu Ser Ser Asp
1               5                   10                  15

Gln Asn Phe Asp Tyr Met Phe Lys Ile Leu Ile Ile Gly Asn Ser Ser
            20                  25                  30

Val Gly Lys Thr Ser Phe Leu Phe Arg Tyr Ala Asp Ser Phe Thr
        35                  40                  45

Pro Ala Phe Val Ser Thr Val Gly Ile Asp Phe Lys Val Lys Thr Ile
    50                  55                  60

Tyr Arg Asn Asp Lys Arg Ile Lys Leu Gln Ile Trp Asp Thr Ala Gly
65                  70                  75                  80

Gln Glu Arg Tyr Arg Thr Ile Thr Thr Ala Tyr Tyr Arg Gly Ala Met
                85                  90                  95

Gly Phe Ile Leu Met Tyr Asp Ile Thr Asn Glu Glu Ser Phe Asn Ala
            100                 105                 110

Val Gln Asp Trp Ser Thr Gln Ile Lys Thr Tyr Ser Trp Asp Asn Ala
        115                 120                 125

```
Gln Val Leu Val Gly Asn Lys Cys Asp Met Glu Asp Glu Arg Val
        130                 135                 140

Val Ser Ser Glu Arg Gly Arg Gln Leu Ala Asp His Leu Gly Phe Glu
145                 150                 155                 160

Phe Phe Glu Ala Ser Ala Lys Asp Asn Ile Asn Val Lys Gln Thr Phe
                165                 170                 175

Glu Arg Leu Val Asp Val Ile Cys Glu Lys Met Ser Glu Ser Leu Asp
                180                 185                 190

Thr Ala Asp Pro Ala Val Thr Gly Ala Lys Gln Gly Pro Gln Leu Ser
                195                 200                 205

Asp Gln Gln Val Pro Pro His Gln Asp Cys Ala Cys
                210                 215                 220

<210> SEQ ID NO 21
<211> LENGTH: 219
<212> TYPE: PRT
<213> ORGANISM: Homo sapiens

<400> SEQUENCE: 21

Met Ala Ser Ala Gly Asp Thr Gln Ala Gly Pro Arg Asp Ala Ala Asp
1               5                   10                  15

Gln Asn Phe Asp Tyr Met Phe Lys Leu Leu Leu Ile Gly Asn Ser Ser
                20                  25                  30

Val Gly Lys Thr Ser Phe Leu Phe Arg Tyr Ala Asp Asp Ser Phe Thr
            35                  40                  45

Pro Ala Phe Val Ser Thr Val Gly Ile Asp Phe Lys Val Lys Thr Val
        50                  55                  60

Tyr Arg His Asp Lys Arg Ile Lys Leu Gln Ile Trp Asp Thr Ala Gly
65                  70                  75                  80

Gln Glu Arg Tyr Arg Thr Ile Thr Thr Ala Tyr Tyr Arg Gly Ala Met
                85                  90                  95

Gly Phe Leu Leu Met Tyr Asp Ile Ala Asn Gln Glu Ser Phe Ala Ala
            100                 105                 110

Val Gln Asp Trp Ala Thr Gln Ile Lys Thr Tyr Ser Trp Asp Asn Ala
        115                 120                 125

Gln Val Ile Leu Val Gly Asn Lys Cys Asp Leu Glu Asp Glu Arg Val
    130                 135                 140

Val Pro Ala Glu Asp Gly Arg Arg Leu Ala Asp Asp Leu Gly Phe Glu
145                 150                 155                 160

Phe Phe Glu Ala Ser Ala Lys Glu Asn Ile Asn Val Lys Gln Val Phe
                165                 170                 175

Glu Arg Leu Val Asp Val Ile Cys Glu Lys Met Asn Glu Ser Leu Glu
                180                 185                 190

Pro Ser Ser Ser Gly Ser Asn Gly Lys Gly Pro Ala Val Gly Asp
                195                 200                 205

Ala Pro Ala Pro Gln Pro Ser Ser Cys Ser Cys
                210                 215

<210> SEQ ID NO 22
<211> LENGTH: 206
<212> TYPE: PRT
<213> ORGANISM: Homo sapiens
```

<400> SEQUENCE: 22

```
Met Asp Glu Asp Val Leu Thr Thr Leu Lys Ile Leu Ile Ile Gly Glu
1               5                   10                  15
Ser Gly Val Gly Lys Ser Ser Leu Leu Leu Arg Phe Thr Asp Asp Thr
            20                  25                  30
Phe Asp Pro Glu Leu Ala Ala Thr Ile Gly Val Asp Phe Lys Val Lys
        35                  40                  45
Thr Ile Ser Val Asp Gly Asn Lys Ala Lys Leu Ala Ile Trp Asp Thr
    50                  55                  60
Ala Gly Gln Glu Arg Phe Arg Thr Leu Thr Pro Ser Tyr Tyr Arg Gly
65                  70                  75                  80
Ala Gln Gly Val Ile Leu Val Tyr Asp Val Thr Arg Arg Asp Thr Phe
                85                  90                  95
Val Lys Leu Asp Asn Trp Leu Asn Glu Leu Glu Thr Tyr Cys Thr Arg
            100                 105                 110
Asn Asp Ile Val Asn Met Leu Val Gly Asn Lys Ile Asp Lys Glu Asn
        115                 120                 125
Arg Glu Val Asp Arg Asn Glu Gly Leu Lys Phe Ala Arg Lys His Ser
    130                 135                 140
Met Leu Phe Ile Glu Ala Ser Ala Lys Thr Cys Asp Gly Val Gln Cys
145                 150                 155                 160
Ala Phe Glu Glu Leu Val Lys Ile Ile Gln Thr Pro Gly Leu Trp
                165                 170                 175
Glu Ser Glu Asn Gln Asn Lys Gly Val Lys Leu Ser His Arg Glu Glu
            180                 185                 190
Gly Gln Gly Gly Gly Ala Cys Gly Gly Tyr Cys Ser Val Leu
        195                 200                 205
```

<210> SEQ ID NO 23
<211> LENGTH: 215
<212> TYPE: PRT
<213> ORGANISM: Homo sapiens

<400> SEQUENCE: 23

```
Met Ala Ser Arg Gly Ala Thr Arg Pro Asn Gly Pro Asn Thr Gly Asn
1               5                   10                  15
Lys Ile Cys Gln Phe Lys Leu Val Leu Leu Gly Glu Ser Ala Val Gly
            20                  25                  30
Lys Ser Ser Leu Val Leu Arg Phe Val Lys Gly Gln Phe His Glu Phe
        35                  40                  45
Gln Glu Ser Thr Ile Gly Ala Ala Phe Leu Thr Gln Thr Val Cys Leu
    50                  55                  60
Asp Asp Thr Thr Val Lys Phe Glu Ile Trp Asp Thr Ala Gly Gln Glu
65                  70                  75                  80
Arg Tyr His Ser Leu Ala Pro Met Tyr Tyr Arg Gly Ala Gln Ala Ala
                85                  90                  95
Ile Val Val Tyr Asp Ile Thr Asn Glu Glu Ser Phe Ala Arg Ala Lys
            100                 105                 110
Asn Trp Val Lys Glu Leu Gln Arg Gln Ala Ser Pro Asn Ile Val Ile
        115                 120                 125
Ala Leu Ser Gly Asn Lys Ala Asp Leu Ala Asn Lys Arg Ala Val Asp
    130                 135                 140
Phe Gln Glu Ala Gln Ser Tyr Ala Asp Asp Asn Ser Leu Leu Phe Met
145                 150                 155                 160
```

```
Glu Thr Ser Ala Lys Thr Ser Met Asn Val Asn Glu Ile Phe Met Ala
                165                 170                 175

Ile Ala Lys Lys Leu Pro Lys Asn Glu Pro Gln Asn Pro Gly Ala Asn
            180                 185                 190

Ser Ala Arg Gly Arg Gly Val Asp Leu Thr Glu Pro Thr Gln Pro Thr
        195                 200                 205

Arg Asn Gln Cys Cys Ser Asn
    210                 215

<210> SEQ ID NO 24
<211> LENGTH: 216
<212> TYPE: PRT
<213> ORGANISM: Homo sapiens

<400> SEQUENCE: 24

Met Ala Gly Arg Gly Ala Ala Arg Pro Asn Gly Pro Ala Ala Gly
1               5                   10                  15

Asn Lys Ile Cys Gln Phe Lys Leu Val Leu Leu Gly Glu Ser Ala Val
                20                  25                  30

Gly Lys Ser Ser Leu Val Leu Arg Phe Val Lys Gly Gln Phe His Glu
            35                  40                  45

Tyr Gln Glu Ser Thr Ile Gly Ala Ala Phe Leu Thr Gln Thr Val Cys
    50                  55                  60

Leu Asp Asp Thr Thr Val Lys Phe Glu Ile Trp Asp Thr Ala Gly Gln
65                  70                  75                  80

Glu Arg Tyr His Ser Leu Ala Pro Met Tyr Tyr Arg Gly Ala Gln Ala
                85                  90                  95

Ala Ile Val Val Tyr Asp Ile Thr Asn Thr Asp Thr Phe Ala Arg Ala
                100                 105                 110

Lys Asn Trp Val Lys Glu Leu Gln Arg Gln Ala Ser Pro Asn Ile Val
            115                 120                 125

Ile Ala Leu Ala Gly Asn Lys Ala Asp Leu Ala Ser Lys Arg Ala Val
    130                 135                 140

Glu Phe Gln Glu Ala Gln Ala Tyr Ala Asp Asp Asn Ser Leu Leu Phe
145                 150                 155                 160

Met Glu Thr Ser Ala Lys Thr Ala Met Asn Val Asn Glu Ile Phe Met
                165                 170                 175

Ala Ile Ala Lys Lys Leu Pro Lys Asn Glu Pro Gln Asn Ala Thr Gly
            180                 185                 190

Ala Pro Gly Arg Asn Arg Gly Val Asp Leu Gln Glu Asn Asn Pro Ala
        195                 200                 205

Ser Arg Ser Gln Cys Cys Ser Asn
    210                 215

<210> SEQ ID NO 25
<211> LENGTH: 215
<212> TYPE: PRT
<213> ORGANISM: Homo sapiens

<400> SEQUENCE: 25

Met Thr Ser Arg Ser Thr Ala Arg Pro Asn Gly Gln Pro Gln Ala Ser
1               5                   10                  15

Lys Ile Cys Gln Phe Lys Leu Val Leu Leu Gly Glu Ser Ala Val Gly
                20                  25                  30

Lys Ser Ser Leu Val Leu Arg Phe Val Lys Gly Gln Phe His Glu Tyr
            35                  40                  45
```

```
Gln Glu Ser Thr Ile Gly Ala Ala Phe Leu Thr Gln Ser Val Cys Leu
    50                  55                  60

Asp Asp Thr Thr Val Lys Phe Glu Ile Trp Asp Thr Ala Gly Gln Glu
65                  70                  75                  80

Arg Tyr His Ser Leu Ala Pro Met Tyr Tyr Arg Gly Ala Gln Ala Ala
                85                  90                  95

Ile Val Val Tyr Asp Ile Thr Asn Gln Glu Thr Phe Ala Arg Ala Lys
            100                 105                 110

Thr Trp Val Lys Glu Leu Gln Arg Gln Ala Ser Pro Ser Ile Val Ile
            115                 120                 125

Ala Leu Ala Gly Asn Lys Ala Asp Leu Ala Asn Lys Arg Met Val Glu
    130                 135                 140

Tyr Glu Glu Ala Gln Ala Tyr Ala Asp Asp Asn Ser Leu Leu Phe Met
145                 150                 155                 160

Glu Thr Ser Ala Lys Thr Ala Met Asn Val Asn Asp Leu Phe Leu Ala
                165                 170                 175

Ile Ala Lys Lys Leu Pro Lys Ser Glu Pro Gln Asn Leu Gly Gly Ala
            180                 185                 190

Ala Gly Arg Ser Arg Gly Val Asp Leu His Gln Ser Gln Gln Asn
    195                 200                 205

Lys Ser Gln Cys Cys Ser Asn
    210                 215

<210> SEQ ID NO 26
<211> LENGTH: 208
<212> TYPE: PRT
<213> ORGANISM: Homo sapiens

<400> SEQUENCE: 26

Met Ser Thr Gly Gly Asp Phe Gly Asn Pro Leu Arg Lys Phe Lys Leu
1               5                   10                  15

Val Phe Leu Gly Glu Gln Ser Val Gly Lys Thr Ser Leu Ile Thr Arg
                20                  25                  30

Phe Met Tyr Asp Ser Phe Asp Asn Thr Tyr Gln Ala Thr Ile Gly Ile
            35                  40                  45

Asp Phe Leu Ser Lys Thr Met Tyr Leu Glu Asp Arg Thr Ile Arg Leu
    50                  55                  60

Gln Leu Trp Asp Thr Ala Gly Gln Glu Arg Phe Arg Ser Leu Ile Pro
65                  70                  75                  80

Ser Tyr Ile Arg Asp Ser Ala Ala Ala Val Val Val Tyr Asp Ile Thr
                85                  90                  95

Asn Val Asn Ser Phe Gln Gln Thr Thr Lys Trp Ile Asp Asp Val Arg
            100                 105                 110

Thr Glu Arg Gly Ser Asp Val Ile Ile Met Leu Val Gly Asn Lys Thr
            115                 120                 125

Asp Leu Ala Asp Lys Arg Gln Val Ser Ile Glu Glu Gly Glu Arg Lys
    130                 135                 140

Ala Lys Glu Leu Asn Val Met Phe Ile Glu Thr Ser Ala Lys Ala Gly
145                 150                 155                 160

Tyr Asp Val Lys Gln Leu Phe Arg Arg Val Ala Ala Ala Leu Pro Gly
                165                 170                 175

Met Glu Ser Thr Gln Asp Arg Ser Arg Glu Asp Met Ile Asp Ile Lys
            180                 185                 190

Leu Glu Lys Pro Gln Glu Gln Pro Val Ser Glu Gly Gly Cys Ser Cys
            195                 200                 205
```

<210> SEQ ID NO 27
<211> LENGTH: 208
<212> TYPE: PRT
<213> ORGANISM: Homo sapiens

<400> SEQUENCE: 27

Met Ser Ala Gly Gly Asp Phe Gly Asn Pro Leu Arg Lys Phe Lys Leu
1               5                   10                  15

Val Phe Leu Gly Glu Gln Ser Val Gly Lys Thr Ser Leu Ile Thr Arg
            20                  25                  30

Phe Met Tyr Asp Ser Phe Asp Asn Thr Tyr Gln Ala Thr Ile Gly Ile
        35                  40                  45

Asp Phe Leu Ser Lys Thr Met Tyr Leu Glu Asp Arg Thr Val Arg Leu
    50                  55                  60

Gln Leu Trp Asp Thr Ala Gly Gln Glu Arg Phe Arg Ser Leu Ile Pro
65                  70                  75                  80

Ser Tyr Ile Arg Asp Ser Thr Val Ala Val Val Val Tyr Asp Ile Thr
                85                  90                  95

Asn Leu Asn Ser Phe Gln Gln Thr Ser Lys Trp Ile Asp Asp Val Arg
            100                 105                 110

Thr Glu Arg Gly Ser Asp Val Ile Ile Met Leu Ala Gly Asn Lys Thr
        115                 120                 125

Asp Leu Ala Asp Lys Arg Gln Ile Thr Ile Glu Glu Gly Glu Gln Arg
    130                 135                 140

Ala Lys Glu Leu Ser Val Met Phe Ile Glu Thr Ser Ala Lys Thr Gly
145                 150                 155                 160

Tyr Asn Val Lys Gln Leu Phe Arg Arg Val Ala Ser Ala Leu Pro Gly
                165                 170                 175

Met Glu Asn Val Gln Glu Lys Ser Lys Glu Gly Met Ile Asp Ile Lys
            180                 185                 190

Leu Asp Lys Pro Gln Glu Pro Pro Ala Ser Glu Gly Gly Cys Ser Cys
        195                 200                 205

<210> SEQ ID NO 28
<211> LENGTH: 207
<212> TYPE: PRT
<213> ORGANISM: Homo sapiens

<400> SEQUENCE: 28

Met Thr Ser Arg Lys Lys Val Leu Leu Lys Val Ile Ile Leu Gly Asp
1               5                   10                  15

Ser Gly Val Gly Lys Thr Ser Leu Met Asn Gln Tyr Val Asn Lys Lys
            20                  25                  30

Phe Ser Asn Gln Tyr Lys Ala Thr Ile Gly Ala Asp Phe Leu Ile Lys
        35                  40                  45

Glu Val Met Val Asp Asp Arg Leu Val Thr Met Gln Ile Trp Asp Thr
    50                  55                  60

Ala Gly Gln Glu Arg Phe Gln Ser Leu Gly Val Ala Phe Tyr Arg Gly
65                  70                  75                  80

Ala Asp Cys Cys Val Leu Val Phe Asp Val Thr Ala Pro Asn Thr Phe
                85                  90                  95

Lys Thr Leu Asp Ser Trp Arg Asp Glu Phe Leu Ile Gln Ala Ser Pro
            100                 105                 110

Arg Asp Pro Glu Asn Phe Pro Phe Val Val Leu Gly Asn Lys Ile Asp
        115                 120                 125

-continued

```
Leu Glu Asn Arg Gln Val Ala Thr Lys Arg Ala Gln Ala Trp Cys Tyr
    130                 135                 140
Ser Lys Asn Asn Ile Pro Tyr Phe Glu Thr Ser Ala Lys Glu Ala Ile
145                 150                 155                 160
Asn Val Glu Gln Ala Phe Gln Thr Ile Ala Arg Asn Ala Leu Lys Gln
                165                 170                 175
Glu Thr Glu Glu Glu Leu Tyr Asn Glu Phe Pro Glu Pro Ile Lys Leu
            180                 185                 190
Asp Lys Asn Asp Arg Ala Lys Ala Ser Ala Glu Ser Cys Ser Cys
            195                 200                 205
```

METHOD FOR IDENTIFYING AGENTS WHICH MODULATE GTPASE ACTIVITY INVOLVED IN INSULIN-STIMULATED GLUT4 TRANSLOCATION

This application claims benefit of U.S. Provisional Patent Application Ser. No. 60/660,131, filed Mar. 9, 2005, the contents of which is incorporated herein by reference in its entirety.

This invention was made in the course of research sponsored by the National Institutes of Health (Grant No. DK025336). The U.S. government may have certain rights in this invention.

BACKGROUND OF THE INVENTION

Insulin treatment of fat and muscle cells causes a rapid increase in glucose transport. The basis for this effect is an increase of glucose transporters of the GLUT4 type at the cell surface. This increase occurs as the result of insulin-stimulated movement of intracellular vesicles containing GLUT4 to the plasma membrane and fusion therewith, a process known as GLUT4 translocation (Watson, et al. (2004) *Endocrine Rev.* 25:177-204). Evidence suggests that a signaling pathway necessary for GLUT4 translocation is the one that proceeds from the insulin receptor to the activation of the protein kinase B, also referred to as Akt (Watson, et al. (2004) supra; Bae, et al. (2003) *J. Biol. Chem.* 278:49530-49536; Jiang, et al. (2003) *Proc. Natl. Acad. U.S.A.* 100:7569-7574; Katome, et al. (2003) *J. Biol. Chem.* 278:28312-28323). However, there is less information about the connection between Akt activation and GLUT4 translocation. A 160-kDa Akt substrate protein having the properties expected for this connection has been described (Kane, et al. (2002) *J. Biol. Chem.* 277:22115-22118; Sano, et al. (2003) *J. Biol. Chem.* 278:14599-14602). This protein, which has been designated AS160 (Akt substrate of 160-kDa), has a predicted GTPase activating protein (GAP) domain toward members of the Rab protein family.

Rabs are small ras-related GTP-binding proteins that in their GTP-bound form participate in vesicle movement and fusion (Zerial and McBride (2001) *Nat. Rev. Mol. Cell. Biol.* 2:107-119). The GAP for a Rab stimulates the typically slow intrinsic GTPase activity of the Rab, to generate the inactive GDP-bound form of the Rab. AS160 is phosphorylated by insulin-activated Akt suggesting that phosphorylation of AS160 inhibits its GAP activity (Sano, et al. (2003) supra); consequently, the GTP form of a Rab(s) required for GLUT4 translocation is elevated, and thus translocation is triggered. Further, insulin-stimulated GLUT4 translocation in adipocytes was blocked by expression of a mutant of AS160 lacking Akt phosphorylation sites (Sano, et al. (2002) supra). Presumably, this nonphosphorylatable mutant of AS160 continued to function as a GAP in the presence of insulin. This blockage required a functional GAP domain as the nonphosphorylatable mutant was not effective when the catalytic Arginine in the GAP domain was mutated to Lysine.

SUMMARY OF THE INVENTION

The present invention is method for identifying an agent which modulates the GTPase activity of AS160. The method involves contacting a polypeptide comprising the GAP domain of AS160, in the presence of a selected GTP-bound Rab, with a test agent and determining whether said agent modulates the hydrolysis of the Rab-bound GTP to GDP, wherein an agent which modulates the amount or rate of GTP to GDP hydrolysis is indicative of an agent that modulates the GTPase activity of AS160.

BRIEF DESCRIPTION OF THE DRAWINGS

FIG. 1 depicts an amino acid sequence alignment of Rab proteins Rab2A (2A), Rab8A (8A), Rab8B (8B), Rab10 (10), and Rab14 (14) selected for being activated by the GAP domain of AS160. Underlined amino acid residues are common amongst Rabs 2A, 8A, 8B, 10, and 14 and together form a cluster unique among all the Rabs found in GLUT4 vesicles and serving as GAP substrates. Symbols in the consensus sequence are as follows: x denotes any amino acid residue; ! denotes Ile or Val; $ denotes Leu or Met; % denotes Phe or Tyr; and # denotes Asn, Asp, Gln, or Glu. Secondary structural units (α helices and β sheets) of Rab GTPases are indicated above the sequences whereas highly conserved motifs are in bold with guanine-base-binding motif indicated with a G and phosphate/magnesium-binding motifs indicated with a PM. See Stenmark and Olkkonen (2001) *Genome Diol.* 2(5): reviews 3007.1-3007.7.

FIGS. 2A-C depict an amino acid sequence alignment of Rab proteins analyzed for activation by the GAP domain of AS160. Underlined and bold amino acid residues are common amongst Rabs 2A, 8A, 8B, 10, and 14 and together form a cluster unique among the Rabs found in GLUT4 vesicles and serving as GAP substrates.

DETAILED DESCRIPTION OF THE INVENTION

Members of the mammalian family of Rab proteins (Zerial and McBride (2001) supra; Pereira-Leal and Seabra (2001) *J. Mol. Biol.* 313:889-901) participate in a specific trafficking step, i.e., recycling endosomes to the plasma membrane. It has now been appreciated that there is a small subset of selected Rab proteins, namely Rab2A, Rab8A, Rab8B, Rab10 and Rab14, serving as substrates for the GAP domain of AS160. The location of these selected Rab proteins on GLUT4 vesicles is indicative of their involvement in GLUT4 translocation.

GLUT4 vesicles were isolated from the low-density microsome fraction of 3T3-L1 adipocytes by immunoadsorption with an antibody against GLUT4, and negative control immunoadsorption was also performed with irrelevant antibody. Vesicle proteins were separated by SDS-PAGE on a short gel, and the proteins in the 21-kDa to 38-kDa region were identified by mass spectrometry. This region encompasses the sizes of almost all Rab proteins, which typically have a size of approximately 25 kDa (Pereira-Leal and Seabra (2001) supra).

By this approach, tryptic peptides from the following Rab proteins were found in GLUT4 vesicles: 1A, 1B, 2A, 3A or 3D, 4B, 5A, 5B, 5C, 6A or 6B, 7, 8A or 8B, 10, 11B, 14, 18, and 35. Some of the Rab proteins listed as two possibilities, such as Rab3A or Rab3B, were tryptic peptides common to both members of the Rab subfamily. In some cases, both peptides common to a Rab subfamily (for example, Rab2A and Rab2B) and ones specific to a member of the subfamily (for example, Rab2A) were found. Using immunoblot analysis, GLUT4 vesicles have been previously found to contain Rabs 4 and 11 (Cormont, et al. (1993) *J. Biol. Chem.* 268: 19491-19497; Kessler, et al. (2000) *Diabetologia* 43:1518-1527).

Unexpectedly, the negative control for GLUT4 vesicle preparation also yielded peptides from all the Rabs present in the GLUT4 vesicles, with the exception of Rabs 1A, 1B, 5A, and 35. Two reasons could account for the large number of Rabs common to both the GLUT4 vesicles and the negative control: a small amount of GLUT4 vesicles may have bound to the irrelevant adsorbent, or some non-GLUT4 vesicles may have bound to the anti-GLUT4 adsorbent as well as to the irrelevant adsorbent. The sensitivity of microcapillary liquid-chromatography tandem mass spectrometry resulted in the detection of these minor impurities as it does not give a measure of amounts, only of identity. Thus, the group of Rabs found in the GLUT4 vesicle preparation includes most, if not all, the Rabs in vesicles with GLUT4, as well as some Rabs that are not in such vesicles. Nonetheless, these results allowed for the selection of Rabs to test as substrates for AS160 GAP domain.

An AS160 GAP domain-GST fusion protein was prepared, as were GST fusion proteins of one or more members of each subfamily of Rab found in the GLUT4 vesicle preparation and several other Rabs implicated in exocytosis in other systems. The activity of the GAP domain was assayed by measuring its effect on the rate of conversion of the GTP form of each GST-Rab to the GDP form. This assay required that the recombinant GST-Rab be functional in binding GTP. Table 1 lists the Rabs used in this assay and summarizes the results from the assay for $[\alpha^{32}P]$GTP loading of each of the Rabs.

TABLE 1

| Rab | % GTP bound | Rab | % GTP bound |
| --- | --- | --- | --- |
| 1A | 43 | 10 | 40 |
| 2A | 50 | 11A | 48 |
| 3A | 43 | 11B | 33 |
| 4A | 58 | 14 | 42 |
| 4B | 57 | 18 | 25 |
| 5A | 45 | 21 | 43 |
| 6 | 29 | 27A | 27 |
| 7 | 48 | 27B | 70 |
| 8A | 50 | 35 | 33 |
| 8B | 40 | | |

In the case of Rab5A, GTP binding was conducted for 1 minute, rather than the 30 minutes used for other Rab proteins, because longer times resulted in considerable hydrolysis of GTP to GDP.

Each Rab specifically bound GTP, ranging from a high of 70%, to a low of 25%. The lowest GTP loading was sufficient for determining whether the GAP domain stimulated the hydrolysis of Rab-bound $[\alpha^{32}P]$GTP.

The rate of conversion of the $[\alpha^{32}P]$GTP form of the Rab to the $[\alpha^{32}P]$GDP form was measured in the presence and absence of the GAP domain through separation of the GTP from GDP by thin layer chromatography. To be certain that the GTPase activity was due to the GAP domain, a point mutant of the GST-GAP domain was generated in which Arg$^{973}$, predicted to be required for activity (Will, et al. (2001) J. Biol. Chem. 276:12135-12139), was mutated to Lys. This mutation is known to affect AS160 function in vivo (Sano, et al. (2003) supra). This mutated GAP domain (designated GAP Arg/Lys) showed no activity against Rab14, one of the Rabs against which the AS160 GAP domain is active.

Further, neither the GST-GAP domain nor the GST-GAP Arg/Lys exhibited significant hydrolytic activity against $[\alpha^{32}P]$GTP alone (i.e., not bound to a Rab). Since GST fusion proteins are known to exist as dimers, it was also determined whether the activity of the GAP domain against Rab14 could be dependent upon formation of a heterodimer composed of one subunit of GST-GAP and one subunit of GST-Rab14. To test this possibility, the GTP conversion assay was carried out in the presence of GST, rather than BSA, as the carrier protein. GST was added at a 10-fold molar excess over the combined GST-GAP and GST-Rab14. If heterodimerization were required for GAP activity, the GST would be expected to inhibit the activity markedly, since it should be preferred as the partner in the heterodimers due to its higher concentration. However, the presence of excess GST did not inhibit the GAP activity. In addition, the activity of the recombinant GST-GAP domain was compared with that of recombinant GAP domain without GST against Rab14, and no difference was observed. The recombinant GAP domain without GST was prepared from recombinant GST-GAP domain bound to immobilized glutathione by thrombin cleavage at the thrombin site in the linker between the GST and GAP domain.

The results of the Rab-bound GTP hydrolysis assay in the presence of the AS160 GAP domain indicated that the GAP domain markedly stimulated the hydrolysis of $[\alpha^{32}P]$GTP bound to Rabs 2A, 8A, 8B, 10, and 14. In a neighbor joining tree defining the relatedness of mammalian Rabs, Rabs 2A and 14 are closely related, as are Rabs 8A, 8B, and 10 (Pereira-Leal and Seabra (2001) J. Mol. Biol. 313:889-901). For each of Rab 2A, 8A, 8B, 10, and 14, the GAP Arg/Lys construct exhibited no significant activity. Moreover, it was noted that the intrinsic GTPase activity of the Rabs varied considerably. For example, after correction for the fraction of GTP bound to the Rab (Table 1), Rab7 showed only 4% of hydrolysis of its bound GTP in 15 minutes at 30° C., whereas Rab3A showed 60% hydrolysis of its bound GTP in 15 minutes.

At the concentration of GST-GAP domain used in the assay, the activities toward Rab 2A, 8A, 8B, 10, and 14 were such that the percentage of the $[\alpha^{32}P]$GTP hydrolyzed in the initial 15 minute period of the assay were approximately the same as the percentages that were bound to the Rab (Table 1). Since most of the Rab-bound GTP was hydrolyzed, the assay under these conditions did not yield an accurate measure of the GAP activity toward each Rab. To measure the activity more accurately, the assay was performed with lower concentrations of the GST-GAP domain with Rab 2A, 8A, 8B, 10 and 14. At the lower concentrations of the GST-GAP domain, the rate of GTP hydrolysis for each Rab became more linear with time and approximately proportional to the concentration of the GAP domain. The magnitude of activity of the AS160 GAP domain was slightly lower than that reported for other Rab GAPS, but was in the same range. For example, with GST-Rab14 as the substrate, the rate of hydrolysis of the bound $[\alpha^{32}P]$GTP in the assay was approximately 3% per minute with 130 nM GST-GAP domain. Assuming that the low concentration of GST-Rab14-bound GTP (approximately 50 nM) was not saturating, this value corresponds to a $k_{cat}/K_m$ value of 0.2 min$^{-1}$ µmolar$^{-1}$. Only three other mammalian Rab GAPs having a catalytic Arg have been characterized. These are RNTre (Lanzetti, et al. (2000) Nature 408: 374-377) and PR17 (Pei, et al. (2002) Cancer Res. 62:5420-5424), two Rab5 GAPs, and GAPCenA (Cuif, et al. (1999) EMBO J. 18:1772-1782), a Rab6 GAP. Recombinant forms of RNTre, PR17, and GAPCenA GAPs and their Rab substrates yield $k_{cat}/K_m$ values of approximately 2.5, 1.2, and 0.4 min$^{-1}$ µmolar$^{-1}$, respectively. A group of yeast Rab GAP's have been characterized (Will and Gallwitz (2001) J. Biol. Chem. 276:12135-12139) with $k_{cat}/K_m$ values ranging from 1.1 to 42 min$^{-1}$ µmolar$^{-1}$. Thus, the activity of the AS160 GAP domain is between 0.5 and 50% of the values for these other Rab GAPs.

To assess the GAP activity of full-length AS160, recombinant full-length FLAG®-tagged AS160 and the corresponding inactive Arg973Lys mutant were generated in HEK293 cells. The proteins were isolated from nonionic detergent lysates on anti-FLAG® beads and used in the GAP assay at the same molar concentration as had been used for the GST- GAP domain. The full-length AS160 exhibited no significant activity above that of the Arg973Lys mutant with Rabs 2A, 8A, and 14 as substrates. Because it was not possible to release the FLAG®-tagged AS160 from the anti-FLAG® beads in native form, the GAP assay was performed with the full-length proteins attached to the beads with frequent mixing. This difference from the normal assay did not account for the absence of GAP activity, since in a control assay the same molar amount of the GST-GAP domain attached to glutathione beads showed the expected activity against Rab14. The lack of activity of the recombinant full-length AS160 is believed to be due to protein denaturation in the course of its preparation.

GAP domain activity against Rabs 2A, 8A, 8B, 10, and 14 made it of interest to determine whether these Rabs were present in vesicles containing GLUT4. GLUT4 vesicle and control immunoadsorbates from the low density microsomal fraction of unstimulated and insulin-stimulated 3T3-L1 adipocytes were prepared. These fractions were immunoblotted with antibodies against Rab 2, 8, 10, and 14, as well as with an antibody against the insulin-regulated aminopeptidase (IRAP). IRAP is a membrane aminopeptidase that colocalizes with GLUT4 and translocates to the plasma membrane in response to insulin in the same way as GLUT4 (Ross, et al. (1996) *J. Biol. Chem.* 271:3328-3332). As GLUT4 is the same size as the antibody heavy chain, the use of IRAP facilitates this type of analysis.

The IRAP immunoblots showed that GLUT4 vesicles were adsorbed by the anti-GLUT4 adsorbent, but not by the control adsorbent. In addition, the amount of IRAP in the vesicles isolated from insulin-treated cells was about 50% of that in the vesicles from unstimulated cells. This decrease is due to the translocation of IRAP to the plasma membrane. Rab2 was present in the GLUT4 vesicles, but not the control. Rab8 and 10 was enriched in the GLUT4 vesicles relative to the control, which was also positive for Rab8 and 10. Rab14 was present in the GLUT4 vesicles, and the control also showed a faint Rab14 signal. Unlike IRAP, the amounts of Rabs 2, 8, and 10 in the GLUT4 vesicles did not decrease in response to insulin. This finding indicates that Rabs 2, 8, and 10 are in subfractions of GLUT4 vesicles that are not mobilized by insulin. In the case of Rab2, these vesicles may be ones containing GLUT4 in the biosynthetic pathway, since Rab2 is known to participate in trafficking between the endoplasmic reticulum and the Golgi (Tisdale and Balch (1996) *J. Biol. Chem.* 271: 29372-29379). The effect of insulin on the relative amount of Rab14 in GLUT4 vesicles was variable. In one experiment, the amount of Rab14 in GLUT4 vesicles from insulin-treated cells was 50% of that in vesicles from untreated cells, but in two other replicate experiments the amount of Rab14 in GLUT4 vesicles from insulin-treated cells was 75% and 100% of the Rab14 in the vesicles from untreated cells. The presence of lesser amounts of Rab 8, 10 and 14 in the control immunoadsorbates of vesicles may be the result of nonspecific binding of both GLUT4 and other vesicles. When larger amounts of control vesicles were immunoblotted for IRAP, a weak IRAP signal was detected. This result indicates that small amounts of the GLUT4 vesicles bound to the adsorbent with control antibody. These findings are consistent with the detection of many Rabs in the control vesicle immunoadsorbate by mass spectrometry described herein.

AS160 was also found in the GLUT4 vesicles by immunoblot analysis. Although there was some AS160 in the GLUT4 vesicles, most of the AS160 in 3T3-L1 adipocytes is not co-localized with GLUT as determined by immunofluorescence analysis.

These results indicate that the GAP domain of AS160 is functional as a Rab GAP with activity against Rabs 2A, 8A, 8B, 10, and 14. Further, GLUT4 vesicles contain Rabs 2A, 8A or B, 10, and 14, indicating that one or more of these Rabs acts in vivo to control GLUT4 translocation. Rab8 has been implicated in trafficking from the trans-Golgi network and recycling endosomes to the plasma membrane (Ang, et al. (2003) *J. Cell Biol.* 163:339-350). Moreover, Rab8 regulates actin organization (Peränen, et al. (1996) *J. Cell Biol.* 135:153-167) and also the movement of at least one type of vesicles (melanosomes) on actin filaments (Chabrillat, et al. (2005) *Mol. Biol. Cell*). These properties of Rab8 are consistent with a role in GLUT4 translocation, since the GLUT4 vesicles move from the trans-Golgi network/recycling endosome region (Watson, et al. (2004) supra; Shewan, et al. (2003) *Mol. Biol. Cell* 14:973-986) to the plasma membrane, and GLUT4 translocation requires actin remodeling (Watson, et al. (2004) supra). In addition, Rab8 is the mammalian Rab that is most similar to Sec 4p, the yeast Rab that interacts with the yeast exocyst. The exocyst is a plasma membrane complex to which vesicles dock prior to fusion (Hsu, et al. (2004) *Int. Rev. Cytol.* 233:243-265). Mammalian exocyst has been suggested to play a role in the docking of GLUT4 vesicles to the plasma membrane (Inoue, et al. (2003) *Nature* 422:629-633; Ewart, et al. (2005) *J. Biol. Chem.* 280:3812-3816). Rab10 has been localized to the perinuclear region of cells, a region where GLUT4 vesicles also reside (Watson, et al. (2004) supra; Chen, et al. (1993) *Proc. Natl. Acad. Sci. U.S.A.* 90:6508-6512). Rab14 has been localized to both the Golgi and the endosomes (Jununtula, et al. (2004) *Mol. Biol. Cell* 15:2218-2229) and has been suggested to be involved in trafficking between these two organelles. Likewise, GLUT4 has been found to cycle through a subdomain of the trans-Golgi network, and this trafficking pathway has been suggested to participate in insulin-regulated GLUT4 translocation (Shewan, et al. (2003) supra). Thus, by regulating the GTPase activity of AS160, the trafficking and translocation of GLUT4 can be modulated.

Accordingly, the present invention is a method for identifying agents which modulate the GTPase activity of AS160. The method involves contacting a polypeptide containing at least the GAP domain of AS160, in the presence of a selected GTP-bound Rab, with a test agent and determining whether said agent modulates AS160 GAP domain-mediated hydrolysis of the Rab-bound GTP to GDP as compared to a control (e.g., AS160 or the GAP domain thereof and a selected GTP-bound Rab in the absence of a test agent). An agent of the present invention can stabilize or destabilize the Rab-GAP interaction, or stimulate or inhibit the catalytic activity of GAP. An agent which increases or decreases the rate or amount of GTP hydrolyzed to GDP by 10%, 20%, 30%, 40%, 50%, 60%, 70%, or more, will be useful for modulating the activity of AS160. As used in the context of the present invention, a selected GTP-bound Rab is intended to mean Rab2A, Rab8A, Rab8B, Rab10 or Rab14 or fragments thereof which bind GTP and are selected for interacting with and being activated by a polypeptide containing a GAP domain of AS160. Moreover, particular embodiments embrace a Rab protein localized in GLUT4 vesicles. It is contemplated that the assay of the present invention can be conveniently carried in a cell-based or cell-free system with isolated, recombinant proteins (i.e., GAP domain of AS160 in combination with Rab2A, Rab8A, Rab8B, Rab10 or Rab14) as disclosed herein.

In accordance with the instant assay, any suitable polypeptide containing at least the GAP domain of AS160 can be used including polypeptides from human and other mammalian sources as well as full-length AS160 protein or fragments thereof. An exemplary AS160 GAP domain-containing polypeptide is human AS160 protein having an amino acid sequence provided herein as SEQ ID NO:1. In certain embodiments, the instant assay embraces the use of the GAP domain itself identified as amino acid residues 865 to 1299 of SEQ ID NO:1. The amino acid sequence of the GAP domain of AS160 is set forth herein as SEQ ID NO:2.

Rab proteins for use in accordance with the instant assay include Rab2A, Rab8A, Rab8B, Rab10, and Rab14. For example, a suitable human Rab2A protein has an amino acid sequence as set forth in SEQ ID NO:3. See also GENBANK Accession No. AAM21078. Another suitable Rab2A protein can be obtained from *Canis familiaris* (GENBANK Accession No. P61105). An exemplary human Rab8A protein has an amino acid sequence as set forth in SEQ ID NO:4. See also, GENBANK Accession No. CAG47070. Another suitable Rab8A protein can be obtained from *Canis familiaris* (GENBANK Accession No. NP_001003152) or *Macaca fascicularis* (GENBANK Accession No. Q4R5P1). A suitable human Rab8B protein has an amino acid sequence as set forth in SEQ ID NO:5. See also, GENBANK Accession No. NP_057614. Another suitable Rab 8B protein can be obtained from *Rattus norvegicus* (GENBANK Accession No. NP_695229) or *Mus musculus* (GENBANK Accession No. NP_775589). An exemplary human Rab10 protein for use in accordance with the method of the present invention has an amino acid sequence as set forth in SEQ ID NO:6. See also, GENBANK Accession No. NP_057215. Other suitable Rab10 proteins can be obtained from *Canis familiaris* (GENBANK Accession No. NP_001003277) or *Rattus norvegicus* (GENBANK Accession No. NP_059055). A suitable human Rab14 protein has an amino acid sequence as set forth in SEQ ID NO:7. See also, GENBANK Accession No. NP_057406. Other suitable Rab14 proteins can be obtained from *Rattus norvegicus* (GENBANK Accession No. P61107) or *Mus musculus* (GENBANK Accession No. NP_080973).

In particular embodiments, the Rab protein employed in the instant method has an amino acid sequence which contains Cys-21, Ile-55, Lys-56, Leu-57, Gln-58, Ile-59, Trp-60, Asp-61, Thr-62, Ala-63, Gly-64, Gln-65, Glu-66, Val-85, Tyr-86, Asp-87, Ile-88, Thr-89, Gly-142, Ala-159, Phe-160, and Ala-164, wherein the indicated Rab amino acid positions are in reference to the selected Rab consensus sequence set forth herein as SEQ ID NO:8 or in reference to Rab2A (SEQ ID NO:3), said consensus sequence being identified by alignment of human Rab2A (SEQ ID NO:3), Rab8A (SEQ ID NO:4), Rab8B (SEQ ID NO:5), Rab10 (SEQ ID NO:6) and Rab14 (SEQ ID NO:7) (FIG. 1). As depicted in FIGS. 2A-2C, this combination of amino acid residues are common amongst Rab2A, 8A, 8B, 10 and 14, and not commonly found in other Rab protein family members analyzed herein.

Methods for producing recombinant proteins in vivo (i.e., cell-based) are well-established in the art and provided herein. In general, nucleic acids encoding the protein of interest are incorporated into a recombinant expression vector in a form suitable for expression of the protein in a host cell. A suitable form for expression provides that the recombinant expression vector includes one or more regulatory sequences operatively-linked to the nucleic acids encoding the protein of interest in a manner which allows for transcription of the nucleic acids into mRNA and translation of the mRNA into the protein. Regulatory sequences can include promoters, enhancers and other expression control elements (e.g., polyadenylation signals). Such regulatory sequences and vectors encoding the same are known to those skilled in the art and are described in Goeddel, Gene Expression Technology: Methods in Enzymology 185, Academic Press, San Diego, Calif. (1990). Suitable vectors for recombinant protein expression in mammalian, yeast, or prokaryotic systems are commercially available from such sources as STRATAGENE®, INVITROGEN™, Pharmacia and the like. Many of these vectors encode heterologous polypeptides, i.e. signal sequences for secretion and/or other polypeptide which will aid in the purification of the protein of interest. Preferably, the heterologous polypeptide has a specific cleavage site to remove the heterologous polypeptide from the protein of interest. Other useful heterologous polypeptides which can be fused to the protein of interest are those which increase expression or solubility of the fusion protein or aid in the purification of the fusion protein by acting as a ligand in affinity purification. Typical fusion expression vectors include those exemplified herein as well as pMAL (New England Biolabs, Beverly, Mass.) and pRIT5 (Pharmacia, Piscataway, N.J.) which fuse maltose E binding protein, or protein A, respectively, to the protein of interest. It should be understood that the design of the expression vector may depend on such factors as the choice of the host cell to be transfected and/or the level of expression required.

Test agents which can be screened in accordance with the screening assay provided herein encompass numerous chemical classes, though typically they are organic molecules, preferably small organic compounds having a molecular weight of more than 100 and less than about 2,500 daltons. Libraries of such compounds can contain either collections of pure agents or collections of agent mixtures. Examples of pure agents include, but are not limited to, proteins, antibodies, peptides, peptide aptamers, nucleic acids, oligonucleotides, carbohydrates, lipids, synthetic or semi-synthetic chemicals, and purified natural products. Such libraries are commercially available to the skilled artisan. Examples of agent mixtures include, but are not limited to, extracts of prokaryotic or eukaryotic cells and tissues, as well as fermentation broths and cell or tissue culture supernates. In the case of agent mixtures, the methods of this invention are not only used to identify those crude mixtures that possess the desired activity, but also provide the means to monitor purification of the active agent from the mixture for characterization and development as a therapeutic drug. In particular, the mixture so identified can be sequentially fractionated by methods commonly known to those skilled in the art which can include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained.

Library screening can be performed in any format that allows rapid preparation and processing of multiple reactions. Stock solutions of the test agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay, i.e., conversion of GTP to GDP. The detection of the conversion of GTP to GDP can be carried out using standard methods such as radioisotope labeled GTP or fluorescent labeling of GTP (e.g., BODIPY® FL GTP; see, Jameson, et al. (2005) J. Biol. Chem. 280:7712-7719).

A variety of other reagents may be included in the screening assay of the instant invention. These include reagents like salts, neutral proteins, e.g., albumin, detergents, etc. which can be used to facilitate optimal protein-protein binding and/ or reduce non-specific or background interactions. Also, reagents that otherwise improve the efficiency of the assay, such as protease inhibitors, nuclease inhibitors, anti-microbial agents, and the like may be used. The mixture of components may be added in any order that provides for the requisite binding.

In one embodiment of the present invention, an agent which decreases the GTPase activity of AS160 is an antibody or a fragment thereof which specifically binds to AS160 and inhibits the activity thereof. Such an antibody can be monoclonal or polyclonal and can be generated by immunizing an animal with an oligopeptide, peptide, or fragment, e.g., a portion of the GAP domain of AS160. Generally, AS160 oligopeptides, peptides, or fragments have an amino acid sequence consisting of at least five amino acids and more desirably at least 10 amino acids. Fragments of an AS160 protein can be generated by, for example, tryptic digestion and extraction from a preparative SDS-PAGE gel or by recombinant fragment expression and purification. Further, short stretches of amino acids of an AS160 antigen of the invention can be fused with those of another protein such as keyhole limpet hemocyanin and antibody produced against the chimeric molecule. A particularly suitable portion of the GAP domain of AS160 to which an antibody can be raised for specific binding is Leu-Val-Asp-Leu-Gly-Arg-Thr-Phe-Pro-Thr-His-Pro (SEQ ID NO:9), wherein the underlined arginine is critical for GAP activity.

Monoclonal antibodies to an AS160 protein can be prepared using any technique which provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256:495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell. Biol.* 62:109-120).

In addition, techniques developed for the production of humanized and chimeric antibodies, the splicing of mouse antibody genes to human antibody genes to obtain a molecule with appropriate antigen specificity and biological activity, can be used (Morrison, et al. (1984) *Proc. Natl. Acad. Sci.* 81, 6851-6855; Neuberger, et al. (1984) *Nature* 312:604-608; Takeda, et al. (1985) *Nature* 314:452-454). Alternatively, techniques described for the production of single chain antibodies can be adapted, using methods known in the art, to produce specific single chain antibodies. Antibodies with related specificity, but of distinct idiotypic composition, can be generated by chain shuffling from random combinatorial immunoglobulin libraries (Burton (1991) *Proc. Natl. Acad. Sci.* 88, 11120-11123).

Antibodies can also be produced by inducing in vivo production in the lymphocyte population or by screening immunoglobulin libraries or panels of highly specific binding reagents as is well-known in the art (Orlandi, et al. (1989) *Proc. Natl. Acad. Sci.* 86: 3833-3837; Winter, et al. (1991) *Nature* 349:293-299).

Antibody fragments, which contain specific binding sites for an AS160 protein, or a fragment thereof, can also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed to allow rapid and easy identification of monoclonal Fab fragments with the desired specificity (Huse, et al. (1989) *Science* 254:1275-1281).

Various immunoassays can be used for screening to identify antibodies, or fragments thereof, having the desired specificity for an AS160 protein or fragment thereof. Numerous protocols for competitive binding (e.g, ELISA), latex agglutination assays, immunoradiometric assays, and kinetics (e.g., BIACOR™ analysis) using either polyclonal or monoclonal antibodies, or fragments thereof, are well-known in the art. Such immunoassays typically involve the measurement of complex formation between a specific antibody and its cognate antigen.

Alternatively, or in conjunction with empirical library screening, AS160 or the GAP domain thereof can be used to generate a crystal structure or virtual three-dimensional structure, whereby a potential inhibitor or activator can be examined through the use of computer modeling using a docking program such as GRAM, DOCK, or AUTODOCK (Dunbrack, et al. (1997) *Folding & Design* 2:27-42). The production and determination of the crystal structure of a GAP domain is well-established in the art. See, e.g., Rak, et al. (2000) *EMBO J.* 19:5105-5113 which teach the crystal structure of the GAP domain of Gyp1p. Like AS160, the GAP domain of Gyp1p has an Arg residue which is essential for the GAP activity, the GAP domain of Gyp1p is 21% identical/38% similar to the sequence of the GAP domain of AS160, and the virtual three-dimensional structure of the GAP domain of AS160 is similar to that of Gyp1p (Matsumoto, et al. (2004) *FEBS Lett.* 572(1-3):135-40). Therefore, it is contemplated that the virtual three-dimensional structure of the Gyp1p/AS160 GAP domain can be used in the identification of agents which modulate the GTPase activity of AS160. Using the virtual three-dimensional structure or crystal structure of the GAP domain of AS160, computer fitting of potential ligands for AS160 is conducted to ascertain how well the shape and the chemical structure of the potential ligand will complement or interfere with, the binding of the GAP domain with a selected GTP-bound Rab. The National Cancer Institute provides calculated structures for about 140,000 of its compounds and MDL Inc. sells the Available Chemicals Directory (ACD) of commercially available compounds. To use these libraries in docking screens, molecular properties such as protonation, charge, stereochemistry, accessible conformations, attraction, repulsion, steric hindrance and salvation are calculated. Generally the tighter the fit (e.g., the lower the steric hindrance, and/or the greater the attractive force) the more potent the potential agent will be since these properties are consistent with a tighter binding constraint. Furthermore, the more specificity in the design of a potential agent the more likely that the agent will not interfere with related mammalian proteins. This will minimize potential side-effects due to unwanted interactions with other proteins.

The immediate effect of insulin secretion is to induce the uptake of glucose by muscle and fat by causing the trafficking of GLUT4 to the plasma membrane. Under pathological conditions, GLUT4 trafficking is blunted. In certain forms of diabetes there is a defect in trafficking of GLUT4 to the cell surface. Thus, AS160 GAP activity inhibitors identified in accordance with the screening method of the instant invention will be useful for restoring or stimulating delivery of GLUT4 to the plasma membrane under conditions where cells are not responding normally to insulin. Such agents would cause increased uptake of glucose into muscle and fat cells thereby lowering the blood glucose concentration.

The invention is described in greater detail by the following non-limiting examples.

Example 1

Plasmids

Plasmids harboring nucleic acids encoding human Rab1A, human Rab4A, human Rab5A, human Rab6, dog Rab7, dog Rab11A, mouse Rab11B, and human Rab21, are well-known in the art. The pGEX plasmids for mouse Rab3A, human Rab4B, dog Rab8A, human Rab10, mouse Rab14, human Rab18, mouse Rab27A, mouse Rab27B, and human Rab35 were prepared by PCR amplification of the Rab coding sequences with templates from several sources, followed by ligation into the PGEX vector. Plasmids encoding N-terminal FLAG®-tagged AS160 and the R973K mutant are known in the art (Kane, et al. (2002) supra). The pGEX plasmids for the GAP domain of AS160 and the R973K mutant GAP were generated by PCR amplification of the DNA encoding GAP domain (i.e., amino acid 865-1299 of human AS160; GENBANK Accession No. gi7662198; Kurihara, et al. (2002) Genomics 79(2):154-161) and ligation into the vector.

Example 2

Antibodies

Antibody to Rab 2 was purchased from Santa Cruz Biotechnology (Santa Cruz, Calif.). Antibody to Rab 8, which reacts with both Rab 8A and 8B, was obtained from BD Transduction Laboratories (San Jose, Calif.). The antibodies against the carboxy-terminus of GLUT4 and the cytoplasmic domain of IRAP are known (Calderhead, et al. (1990) *J. Biol. Chem.* 265:13800-13808; Keller, et al. (1995) *J. Biol. Chem.* 270:23612-23618). An antibody against a peptide corresponding to amino acids 167-183 of mouse Rab 14 was generated by immunization of rabbits with the conjugated peptide (Biosource International, Camarillo, Calif.) followed by affinity purification on the immobilized peptide. An antibody against a peptide corresponding to amino acids 171-186 of mouse Rab10 was generated by immunization of rabbits with the conjugated peptide (21$^{st}$ Century Biochemicals, Marlboro, Mass.) followed by affinity purification on the immobilized peptide.

Example 3

GLUT4 Vesicles

Isolation of GLUT4 vesicles was according to standard methods (Cain, et al. (1992) *J. Biol. Chem.* 267:11681-11684), with slight modifications. 3T3-L1 adipocytes in serum-free medium were treated with 160 nM insulin or not for 30 minutes. Cells on a 10-cm plate were washed with phosphate-buffered saline (PBS) and then with buffer A (1 mM EDTA, 225 mM sucrose, 20 mM HEPES, pH 7.4). Cells were then scraped into 1 mL buffer A with protease inhibitors (10 μM each of leupeptin, pepstatin, and EP475) and homogenized at 20° C. Subsequent steps were at 4° C. The homogenate was centrifuged at 16,000×g for 15 minutes, and the supernatant centrifuged again at 48,000×g for 15 minutes. The supernatant from the second centrifugation, which is a low density microsome/cytosol fraction, was made 100 mM in NaCl and then incubated for 2 hours with anti-GLUT4 or control rabbit immunoglobulin bound to PANSORBIN® (Calbiochem, San Diego, Calif.) (10 μg antibody on 4 μL PANSORBIN® per mL). The adsorbent was then washed several times with buffer A, 100 mM NaCl, and then the bound vesicles were solubilized with 0.5% nonaethyleneglycol dodecyl ether in buffer A/100 mM NaCl. For identification of the Rabs by mass spectrometry, SDS samples of the solubilized GLUT4 and control vesicles, each from three 10-cm plates, were separated on a short gradient gel; the gel region containing the Rabs (21-38 kDa section) was excised and analyzed. In-gel tryptic digestion was performed and tryptic peptides were sequenced by microcapillary liquid chromatography tandem mass spectrometry. For immunoblot analysis, vesicle samples were separated by SDS-PAGE, and immunoblotted for specific proteins according to standard methods (Sano, et al. (2003) supra).

Example 4

Recombinant Proteins

The pGEX-Rab plasmids were introduced into *E. coli* strain BL21 or, in the case of GST-Rab 14, into the Rosetta BL21 strain (Novagen, Madison, Wis.). Bacterial cultures (200 mL) were grown to an absorbance of approximately 0.5, and then induced with 0.1 mM isopropyl β-thiogalactopyranoside for 6 hours at 25° C. or overnight at 15° C. The bacteria were pelleted, resuspended in 10 mL 2.5 mM $MgCl_2$ PBS with protease inhibitors (Roche, Indianapolis, Ind.), and lysed in a French press. The lysate was centrifuged at 23,000×g for 45 minutes, and the supernatant was mixed with 300 μL of glutathione beads (Pierce, Rockford, Ill.) for 1 hour at 4° C. The beads were washed with 2.5 mM $MgCl_2$ PBS, and the GST-Rab was eluted three times with 300 μL 10 mM glutathione, 1 mM dithiothreitol, 2.5 mM $MgCl_2$, 20 mM Tris-HCl, pH 8.0. The procedure for expression of the GST-GAP domain was similar, except that the bacteria were lysed in PBS, 5 mM mercaptoethanol with protease inhibitors, and the GST fusion protein was eluted with 20 mM glutathione, 5 mM mercaptoethanol, 150 mM NaCl, 10% glycerol, 100 mM Tris-HCl, pH 8.5. Rab 11B, which was His-tagged, was expressed in the XL-1 Blue strain and purified on immobilized Ni (QIAGEN®, Valencia, Calif.) according to the manufacturer's instructions.

Recombinant FLAG®-tagged AS160 and the R973K mutant thereof were generated by transfecting HEK293 cells with the appropriate AS160 plasmids. Each 10-cm plate was transfected with 10 μg of plasmid using LIPOFECTAMINE® 2000 (INVITROGEN™, Carlsbad, Calif.). After 24 hours, the cells were serum starved for 2 hours, and treated 75 μM of the PI 3-kinase inhibitor LY294002 for the final 45 minutes to deactivate any activated Akt (Basu, et al. (2003) *Mol. Cell.* 11:11-23). The cells were then lysed in 2 mL 1.5% nonethyleneglycol dodecyl ether, 150 mM NaCl, 40 mM HEPES, pH 7.4, with protease inhibitors (10 μM each of pepstatin, leupeptin, aprotinin, and EP475), the lysate was cleared by centrifugation at 12,000×g for 15 minutes, and the AS160 was adsorbed on 10 μL of anti-FLAG® beads (Sigma, St. Louis, Mo.), which were then washed thoroughly with 150 mM NaCl, 40 mM HEPES, pH 7.5. This procedure yielded about 15 μg of AS160 per 10-cm plate.

To estimate the purity and concentration of the recombinant proteins, samples were separated on SDS-PAGE along with known amounts of standard proteins and stained with COOMASSIE® blue. The desired protein was the predominant component in the preparation of each recombinant protein.

Example 5

Assays for Rab GTP Loading and GAP Activity

Loading, as used herein, is the exchange of bound GTP and GDP on recombinant GST-Rab with [$\alpha^{32}$P]GTP; a process facilitated by complexation of magnesium ion with EDTA. Bound [$\alpha^{32}$P]GTP was fixed on the Rab by the addition of Mg ion, and binding was measured by separation of the [$\alpha^{32}$P]GTP complex on a nitrocellulose filter (Liu and Li (1998) *J. Biol. Chem.* 273:10087-10; Ridley, et al. (1993) *EMBO J.* 12:5151-5160). The GST-Rab (1 µM) was incubated at 10-fold molar excess over [$\alpha^{32}$P]GTP (0.1 µM) in 2 mM EDTA, 10 mM glutathione, 1 mM dithiothreitol, 200 µg/mL bovine serum albumin (BSA), 20 mM Tris-HCl, pH 8.0 in a volume of 43.5 µL at 30° C. for 30 minutes. 2.5 µL of 200 mM MgCl$_2$ was added followed by 4 µL of the buffer used for the recombinant GST-GAP domain, so that the conditions for the loading assay were similar to those for the GAP assay. Aliquots (10 µL) of the mixture were filtered through 24-mm nitrocellulose filters (MILLIPORE®, HAWP type), and the filters were washed with 10 mM MgCl$_2$, 2 mM EDTA, 50 mM NaCl, 20 mM Tris-HCl, pH 8.0. The percent of bound GTP was calculated from radioactivity on the filter and the input radioactivity.

The assay used to determine GTP to GDP conversion is well-established (Liu and Li (1998) supra). A GST-Rab was loaded with [$\alpha^{32}$P]GTP as described herein. Immediately after the addition of MgCl$_2$, a 10 µL aliquot was removed as the zero time point. Subsequently, the GST-GAP domain was added in a 4 µL aliquot so that the final concentration was 0.4 µM unless stated otherwise, and incubation was continued at 30° C., with 10 µL aliquots removed at various times. The removed samples were immediately placed in 20 µL 0.2% SDS, 5 mM EDTA, 5 mM GDP, and 5 mM GTP, and held at 65° C. for 2 minutes. Samples (5 µL) were spotted onto a polyethyleneimine cellulose plate, and thin layer chromatography separation was conducted in 0.75 M potassium phosphate, pH 3.5. The radioactivity in the GTP and GDP spots was measured by phosphorimage analysis.

What is claimed is:

1. A method for identifying an agent which modulates the GTPase activity of the Akt substrate of 160-kDa protein (AS160) comprising contacting a polypeptide comprising the GAP domain of AS160, in the presence of a selected GTP-bound Rab, with a test agent and determining whether said agent modulates the hydrolysis of the Rab-bound GTP to GDP, wherein an agent which modulates the amount or rate of GTP to GDP hydrolysis is indicative of an agent that modulates the GTPase activity of AS160.

* * * * *